United States Patent
Stahl et al.

(10) Patent No.: US 10,822,657 B2
(45) Date of Patent: Nov. 3, 2020

(54) METHOD FOR SUCCESSFUL RETRIEVAL OF SPERM

(75) Inventors: Peter J. Stahl, New York, NY (US); Peter N. Schlegel, New York, NY (US); Darius A. Paduch, New York, NY (US)

(73) Assignee: Cornell University, Ithaca, NY (US)

( * ) Notice: Subject to any disclaimer, the term of this patent is extended or adjusted under 35 U.S.C. 154(b) by 648 days.

(21) Appl. No.: 14/005,991

(22) PCT Filed: Mar. 15, 2012

(86) PCT No.: PCT/US2012/029239
§ 371 (c)(1),
(2), (4) Date: Feb. 3, 2014

(87) PCT Pub. No.: WO2012/129048
PCT Pub. Date: Sep. 27, 2012

(65) Prior Publication Data
US 2014/0141420 A1   May 22, 2014

Related U.S. Application Data

(60) Provisional application No. 61/454,283, filed on Mar. 18, 2011.

(51) Int. Cl.
| | | |
|---|---|---|
| *C12Q 1/68* | (2018.01) | |
| *C12Q 1/6881* | (2018.01) | |
| *C12Q 1/6883* | (2018.01) | |
| *G01N 33/68* | (2006.01) | |
| *G01N 33/569* | (2006.01) | |

(52) U.S. Cl.
CPC ......... *C12Q 1/6881* (2013.01); *C12Q 1/6883* (2013.01); *G01N 33/56966* (2013.01); *G01N 33/689* (2013.01); *C12Q 2600/158* (2013.01); *G01N 2333/4706* (2013.01)

(58) Field of Classification Search
None
See application file for complete search history.

(56) References Cited

U.S. PATENT DOCUMENTS

| | | |
|---|---|---|
| 5,871,920 A | 2/1999 | Page et al. |
| 2010/0130859 A1 | 5/2010 | Jarvi |

FOREIGN PATENT DOCUMENTS

| | | |
|---|---|---|
| WO | WO-2012129048 A2 | 9/2012 |
| WO | WO-2012129048 A3 | 1/2013 |

OTHER PUBLICATIONS

Tessari et al; Molecular Human Reproduction, vol. 10, pp. 253-258, 2004.*
Genbank Accession No. BC148445 (NCBI, NLM, 2008).*
Ferlin et al; The Journal of Urology, vol. 183, pp. 1248-1252, Mar. 2010.*
Weikert et al; Cancer Letters, vol. 223, pp. 331-337; 2005.*
"International Application Serial No. PCT/US2012/029239, International Preliminary Report on Patentability dated Oct. 3, 2013", 7 pgs.
"International Application Serial No. PCT/US2012/029239, Search Report dated Oct. 2412", 5 pgs.
"International Application Serial No. PCT/US2012/029239, Written Opinion dated Oct. 2412", 5 pgs.
Stahl, P J, et al., "Heat shock factor Y chromosome (HSFY) mRNA level predicts the presence of retrievable testicular sperm in men with nonobstructive azoospermia", Fertility and Sterility vol. 94 No. 2, (Aug. 2011), 303/308.
Stahl, P J, et al., "Testicular expression analysis of the AZF genses in azoospermic men suggests essentially and specific function for DDX3Y, RPS4Y2, CDY2, and HSFY", Fertility and Sterility vol. 94 S232, (Sep. 2010).
Tessari, A, et al., "Characterization of HSFY, a novel AZFb gene on the Y chromosome with a possible role in human spermatogensis", Molecular Human Reproduction vol. 10 No. 4, (Feb. 16, 2004), 253-258.

* cited by examiner

*Primary Examiner* — Jehanne S Sitton
(74) *Attorney, Agent, or Firm* — Schwegman Lundberg & Woessner, P.A.

(57) ABSTRACT

Measurement of expression levels of heat shock factor Y chromosome (HSFY) in testicular tissue samples or semen can be used to identify whether testicular sperm extraction can be used for patients with all histological variants of nonobstructive azoospermia.

9 Claims, 5 Drawing Sheets

Specification includes a Sequence Listing.

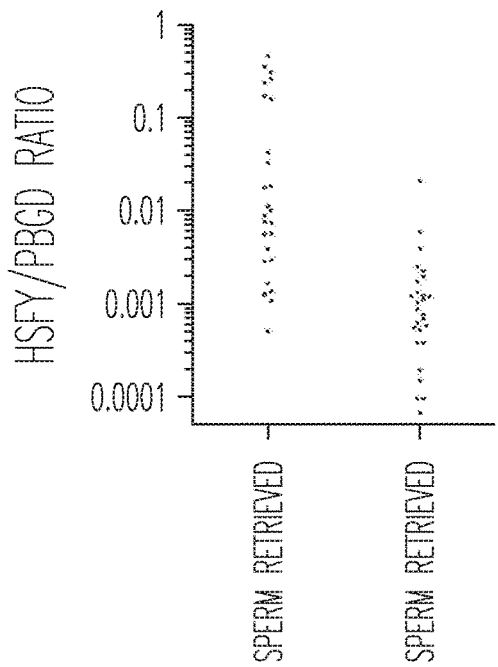

SEQUENCE LISTING

```
<160> NUMBER OF SEQ ID NOS: 8

<210> SEQ ID NO 1
<211> LENGTH: 401
<212> TYPE: PRT
<213> ORGANISM: Homo sapiens

<400> SEQUENCE: 1

Met Ala His Val Ser Ser Glu Thr Gln Asp Val Ser Pro Lys Asp Glu
1               5                   10                  15

Leu Thr Ala Ser Glu Ala Ser Thr Arg Ser Pro Leu Cys Glu His Thr
            20                  25                  30

Phe Pro Gly Asp Ser Asp Leu Arg Ser Met Ile Glu Glu His Ala Phe
        35                  40                  45

Gln Val Leu Ser Gln Gly Ser Leu Leu Glu Ser Pro Ser Tyr Thr Val
    50                  55                  60

Cys Val Ser Glu Pro Asp Lys Asp Asp Phe Leu Ser Leu Asn Phe
65                  70                  75                  80

Pro Arg Lys Leu Trp Lys Ile Val Glu Ser Asp Gln Phe Lys Ser Ile
                85                  90                  95

Ser Trp Asp Glu Asn Gly Thr Cys Ile Val Ile Asn Glu Glu Leu Phe
            100                 105                 110

Lys Lys Glu Ile Leu Glu Thr Lys Ala Pro Tyr Arg Ile Phe Gln Thr
        115                 120                 125

Asp Ala Ile Lys Ser Phe Val Arg Gln Leu Asn Leu Tyr Gly Phe Ser
    130                 135                 140

Lys Ile Gln Gln Asn Phe Gln Arg Ser Ala Phe Leu Ala Thr Phe Leu
145                 150                 155                 160

Ser Glu Glu Lys Glu Ser Ser Val Leu Ser Lys Leu Lys Phe Tyr Tyr
                165                 170                 175

Asn Pro Asn Phe Lys Arg Gly Tyr Pro Gln Leu Leu Val Arg Val Lys
            180                 185                 190

Arg Arg Ile Gly Val Lys Asn Ala Ser Pro Ile Ser Thr Leu Phe Asn
        195                 200                 205

Glu Asp Phe Asn Lys Lys His Phe Arg Ala Gly Ala Asn Met Glu Asn
    210                 215                 220

His Asn Ser Ala Leu Ala Ala Glu Ala Ser Glu Ser Leu Phe Ser
225                 230                 235                 240

Ala Ser Lys Asn Leu Asn Met Pro Leu Thr Arg Glu Ser Ser Val Arg
                245                 250                 255
```

Gln Ile Ile Ala Asn Ser Ser Val Pro Ile Arg Ser Gly Phe Pro Pro
             260                 265                 270

Pro Ser Pro Ser Thr Ser Val Gly Pro Ser Glu Gln Ile Ala Thr Asp
         275                 280                 285

Gln His Ala Ile Leu Asn Gln Leu Thr Thr Ile His Met His Ser His
     290                 295                 300

Ser Thr Tyr Met Gln Ala Arg Gly His Ile Val Asn Phe Ile Thr Thr
305                 310                 315                 320

Thr Thr Ser Gln Tyr His Ile Ile Ser Pro Leu Gln Asn Gly Tyr Phe
                 325                 330                 335

Gly Leu Thr Val Glu Pro Ser Ala Val Pro Thr Arg Tyr Pro Leu Val
             340                 345                 350

Ser Val Asn Glu Ala Pro Tyr Arg Asn Met Leu Pro Ala Gly Asn Pro
         355                 360                 365

Trp Leu Gln Met Pro Thr Ile Ala Asp Arg Ser Ala Ala Pro His Ser
     370                 375                 380

Arg Leu Ala Leu Gln Pro Ser Pro Leu Asp Lys Tyr His Pro Asn Tyr
385                 390                 395                 400

Asn

<210> SEQ ID NO 2
<211> LENGTH: 1443
<212> TYPE: DNA
<213> ORGANISM: Homo sapiens

<400> SEQUENCE: 2
aaccattgtg atggtctaga taagtgtaca tgcttaggcc ttctgaagca gcatttgaag      60
ctgcagtcct gaaaaccatg caggccggaa gagtagataa agaaatattt atttgagatg    120
gcacatgttt cttcagaaac tcaagatgtt tcccccaaag atgaattaac tgcttcagaa    180
gcctccacta ggtctccatt gtgtgaacac accttccctg gggactcaga cttacggtca    240
atgattgaag aacatgcttt tcaggttttg tcacaaggat ccttgttaga aagtccaagt    300
tacacagttt gtgtctctga gccagataaa gatgatgatt ttctttctct gaactttccc    360
aggaaacttt ggaaaatagt ggaaagtgac caattcaagt ctatttcatg ggatgagaat    420
ggaacttgca tagtgattaa tgaagaactc ttcaagaaag aaattttgga aacaaaggct    480
ccttacagaa tatttcaaac tgatgctatc aaaagttttg ttcgacagct caaccttat    540 ggatttagta aaattcaaca gaattttcaa agatctgcct ttctagccac ctttctgtca    600
gaagagaaag aatcgtctgt cttaagcaag ttaaagttct attataatcc aaatttcaag    660
cgtggctatc cccaactttt agtaagagtg aagagaagaa ttggtgttaa aaatgcttca    720
cctatatcta ctttattcaa cgaagatttc aacaagaagc attttagagc agggctaac    780 atggagaatc ataattctgc cttagctgct gaagctagtg aagaaagttt attttcagcc    840
tctaaaaatt taaatatgcc tctaacaagg aatcttctg tcagacagat aattgcaaat    900
tcatctgtcc ccattagaag tggtttccct cctccttcac cttcaacctc agttggacca    960
tcagaacaaa ttgcaacaga tcaacatgct attttaaatc agttgaccac tattcatatg   1020
cactctcata gtacctacat gcaagcaagg ggccacattg tgaattttat acaaccaca   1080 acttctcaat accacatcat atctccctta caaaatggtt attttgggct gacagtggaa   1140
ccatctgctg ttcccacacg atatcctctg gtatcagtca tgaggctcc atatcgtaac   1200 atgctaccag caggcaaccc gtggttgcaa atgcctacga tcgctgatag atcagctgcc   1260

-continued

```
cctcattcca ggctagctct tcaaccatca ccactggaca aatatcaccc taattacaac    1320
tgatctgcca ttaaaagagg accagattat gaatgacaac agagactaac atttacattg    1380
acaaaaaacc ctaaaaattt ctgcaattat cttattgaac aataaaattg catgtttact    1440
tct                                                                  1443
```

<210> SEQ ID NO 3
<211> LENGTH: 203
<212> TYPE: PRT
<213> ORGANISM: Homo sapiens

<400> SEQUENCE: 3

```
Met Ala His Val Ser Ser Glu Thr Gln Asp Val Ser Pro Lys Asp Glu
1               5                   10                  15

Leu Thr Ala Ser Glu Ala Ser Thr Arg Ser Pro Leu Cys Glu His Thr
            20                  25                  30

Phe Pro Gly Asp Ser Asp Leu Arg Ser Met Ile Glu Glu His Ala Phe
        35                  40                  45

Gln Val Leu Ser Gln Gly Ser Leu Leu Glu Ser Pro Ser Tyr Thr Val
    50                  55                  60

Cys Val Ser Glu Pro Asp Lys Asp Asp Phe Leu Ser Leu Asn Phe
65                  70                  75                  80

Pro Arg Lys Leu Trp Lys Ile Val Glu Ser Asp Gln Phe Lys Ser Ile
                85                  90                  95

Ser Trp Asp Glu Asn Gly Thr Cys Ile Val Ile Asn Glu Glu Leu Phe
            100                 105                 110

Lys Lys Glu Ile Leu Glu Thr Lys Ala Pro Tyr Arg Ile Phe Gln Thr
        115                 120                 125

Asp Ala Ile Lys Ser Phe Val Arg Gln Leu Asn Leu Tyr Gly Phe Ser
    130                 135                 140

Lys Ile Gln Gln Asn Phe Gln Arg Ser Ala Phe Leu Ala Thr Phe Leu
145                 150                 155                 160

Ser Glu Glu Lys Glu Ser Ser Val Leu Ser Lys Ile Arg Phe Thr Lys
                165                 170                 175

Met Lys Leu Ser Arg Ser Ser Thr Tyr Glu Asn Arg Tyr Leu Cys Cys
            180                 185                 190

Asn Leu His Leu Lys Asp Glu Ser Asn Tyr Ser
        195                 200
```

<210> SEQ ID NO 4
<211> LENGTH: 1038
<212> TYPE: DNA
<213> ORGANISM: Homo sapiens

<400> SEQUENCE: 4

```
taagtgtaca tgcttaggcc ttctgaagca gcatttgaag ctgcagtcct gaaaaccatg     60
caggccggaa gagtagataa agaaatattt atttgagatg cacatgtttt cttcagaaac    120
tcaagatgtt tccccaaag atgaattaac tgcttcagaa gcctccacta ggtctccatt    180
gtgtgaacac accttccctg gggactcaga cttacggtca atgattgaag aacatgcttt    240
tcaggttttg tcacaaggat ccttgttaga aagtccaagt tacacagttt gtgtctctga    300
gccagataaa gatgatgatt ttctttctct gaactttccc aggaaacttt ggaaaatagt    360
ggaaagtgac caattcaagt ctatttcatg ggatgagaat ggaacttgca tagtgattaa    420
tgaagaactc ttcaagaaag aaattttgga aacaaaggct ccttacagaa tatttcaaac    480
```

```
tgatgctatc aaaagttttg ttcgacagct caacctttat ggatttagta aaattcaaca      540
gaattttcaa agatctgcct ttctagccac ctttctgtca gaagagaaag aatcgtctgt      600
cttaagcaag atacgcttca ccaaaatgaa actttccaga tcttcaactt atgaaaacag      660
gtatttatgt tgcaacttac atttaaaaga tgagtcgaat tactcataat ccttagaagt      720
tagcttgtcc gcatctgaaa attcactttt accttgaagt tcaatctgtc tctgggaaag      780
actagattgg aagaataaaa ttcaagaatg tgatgtttta gtaatggaaa agccaagagc      840
gtcaggtggc aaaagtcctt ctgttactca agaaaatgct ctgaaaaatt cctttctct       900 ttttttttg taaagattaa ctccacctca ccaccacaat gaggtatttt tctcagcaat       960
tgacacctgt ttactcagtt actccctgta actatgttat gctgtgaagt aggcaataca     1020
gttgttaaag aagaataa                                                   1038
```

```
<210> SEQ ID NO 5
<211> LENGTH: 21
<212> TYPE: DNA
<213> ORGANISM: Artificial Sequence
<220> FEATURE:
<223> OTHER INFORMATION: A synthetic primer

<400> SEQUENCE: 5
gtcaatgagg ctccatatcg t                                                 21

<210> SEQ ID NO 6
<211> LENGTH: 20
<212> TYPE: DNA
<213> ORGANISM: Artificial Sequence
<220> FEATURE:
<223> OTHER INFORMATION: A synthetic primer

<400> SEQUENCE: 6
gatcgtaggc atttgcaacc                                                   20

<210> SEQ ID NO 7
<211> LENGTH: 24
<212> TYPE: DNA
<213> ORGANISM: Artificial Sequence
<220> FEATURE:
<223> OTHER INFORMATION: A synthetic primer

<400> SEQUENCE: 7
tcagaagcct ccactaggtc tcca                                              24

<210> SEQ ID NO 8
<211> LENGTH: 25
<212> TYPE: DNA
<213> ORGANISM: Artificial Sequence
<220> FEATURE:
<223> OTHER INFORMATION: A synthetic primer

<400> SEQUENCE: 8
tgacagaaag gtggctagaa aggca                                             25
```

US 10,822,657 B2

METHOD FOR SUCCESSFUL RETRIEVAL OF SPERM

This application is a U.S. National Stage Application filed under 35 U.S.C § 371 of International Application Serial No. PCT/US2012/029239, filed on Mar. 15, 2012 and published as WO 2012/129048 A2 on Sep. 27, 2012, which application claims benefit of the filing date of U.S. Provisional Patent Application No. 61/454,283, filed Mar. 18, 2011, the contents of which applications are specifically incorporated herein in their entirety.

BACKGROUND

The optimal management for enabling a couple in which the male has nonobstructive azoospermia (NOA) to have their own biological offspring via in vitro fertilization involves testicular sperm extraction (TESE) and intracytoplasmic sperm injection (ICSI). However, sperm are absent in the testes of many men with nonobstructive azoospermia, and preoperative clinical parameters cannot reliably predict the presence of retrievable testicular sperm. Microdissection TESE appears to provide sperm retrieval rates (SRR) as high or higher than with conventional TESE or percutaneous sperm retrieval procedures (Schlegel P N, 1999; Tsujimura A, 2004; Ramasamy R, 2005; and Donoso P, 2007), but nonetheless fails in 37-65% of patients with nonobstructive azoospermia (Carpi A, 2006). Men in whom sperm are not retrieved needlessly incur some risk of morbidity, psychological stress, and financial expense. Furthermore, in centers that perform ICSI with freshly retrieved sperm, female partners of men with nonobstructive azoospermia who fail sperm retrieval undergo unnecessary ovarian stimulation and incur its associated risks and inconveniences.

Patients and physicians accept the high failure rates of testicular sperm retrieval in nonobstructive azoospermia (NOA) for two reasons. First, genetic parenthood is such a critical quality of life issue that most affected couples are willing to assume the risks and costs of TESE in spite of the relatively high risk of failure. Secondly, the performance characteristics of available clinical tests to predict TESE outcome are insufficient in almost all cases to preclude an attempt at testicular sperm retrieval. Neither serum hormone assays such as follicle stimulating hormone (FSH) and Inhibin B nor noninvasive assessments such as testicular volume alter the probability of sperm retrieval sufficiently to change clinical management (Carpi et. al. 2009). The only noninvasive method that is helpful in selecting patients for microdissection TESE is Y microdeletion testing. Y microdeletions that involve loss of the complete AZFa or AZFb regions are incompatible with sperm production and are found in 6% of American men with nonobstructive azoospermia (Stahl et. al. 2010). Typically microdissection TESE is not offered to these patients.

Open or percutaneous testicular biopsy for histological assessment is more informative than noninvasive testing and allows for therapeutic sperm retrieval in some cases. Despite being a well-established predictor of microdissection TESE outcome (Su et. al. 1999, Meng et. al. 2000), testicular histology does not change the probability of sperm retrieval enough to affect clinical management among men with nonobstructive azoospermia (NOA). Reported sperm retrieval rates in men with Sertoli cell only (SCO) histology, which is the least favorable histological diagnosis, are 24-48% (Donoso et. al. 2007). At many centers, nearly all of these patients elect to proceed with sperm retrieval given the reasonably high chance of finding sperm. In recognition of the minimal clinical impact of testicular histology amongst men with nonobstructive azoospermia, many fertility centers have abandoned the routine use of preoperative testicular biopsies in these men. Clearly better methods for predicting success of sperm retrieval would have clinical benefit.

SUMMARY

As described herein, the success of retrieving sperm from a male with nonobstructive azoospermia can surprisingly be determined with a high degree of sensitivity and specificity by measuring the levels of expression of the heat shock factor Y chromosome (HSFY) gene in testicular or semen samples. The male can have nonobstructive azoospermia men, including for example, males with all histological variants of nonobstructive azoospermia, particularly those with Sertoli Cell only (SCO) histology. Thus, the methods described herein give greater certainty to whether sperm retrieval, for example, by a microdissection TESE operation can be performed successfully.

Thus, one aspect of the invention relates to a method of evaluating whether to perform testicular sperm extraction in a male. The method involves quantifying HSFY expression in a fluid or tissue sample from the male to provide a quantified HSFY expression level for the male. When the quantified HSFY expression level for the male is higher than baseline quantified HSFY expression levels obtained from men where sperm retrieval failed, sperm can be retrieved from the male.

In one embodiment, the quantified HSFY expression level is measured by quantitative reverse transcription polymerase chain reaction (qRT-PCR). In another embodiment, the quantified HSFY expression level is observed by in situ hybridization probe analysis. In further embodiments, the quantified HSFY expression level is measured by antibody detection procedures.

The fluid or tissue sample from the male can, for example, be semen, urine, blood, testicular tissue or a combination thereof.

The male is a male mammal who has a low sperm count. For example, the male may have nonobstructive azoospermia or any of the histological variants of nonobstructive azoospermia (NOA). In some embodiments, the male is a male exhibiting Sertoli cell only (SCO) histology.

As described herein, HSFY expression levels detected in testis biopsies or semen samples from men with nonobstructive azoospermia predicts the presence of retrievable sperm from men with all histological variants of nonobstructive azoospermia (NOA), particularly those with Sertoli cell only (SCO) histology. Higher HSFY mRNA expression was detected by qRT-PCR and by fluorescence in situ probe analysis in males where sperm retrieval was successful. Detecting the expression levels of HSFY in patients with nonobstructive azoospermia can be used to evaluate and counsel men with nonobstructive azoospermia (NOA).

BRIEF DESCRIPTION OF THE DRAWINGS

FIG. 1A-D illustrate HSFY expression levels for various patient types as a ratio of HSFY to control porphobilinogen-deaminase (PBGD) expression levels. FIG. 1A shows scatter plots illustrating HSFY/PBGD expression ratios for all nonobstructive azoospermia (NOA) patients in the study. FIG. 1B shows scatter plots illustrating HSFY/PBGD expression ratios for all patients with Sertoli Cell only (SCO) histology. FIG. 1C shows scatter plots illustrating HSFY/PBGD expression ratios for all patients with maturation arrest (MA) histology. FIG. 1D shows scatter plots illustrating HSFY/PBGD expression ratios for all patients with hypospermatogenesis (HS) histology. Each dot represents the HSFY/PBGD expression ratio measured in one patient.

FIGS. 3A, C and E are fluorescent micrographs of a representative section of seminiferous tubular tissue from a patient with obstructive azoospermia. FIGS. 3B, D and F are fluorescent micrographs of a representative section of seminiferous tubular tissue from a patient with nonobstructive azoospermia who underwent microdissection TESE, but sperm retrieval failed. FIG. 3A, B: Nuclear counterstaining with DAPI; FIG. 3C, D: HSFY mRNA expression; FIG. 3E, F: overlaid images. 100× magnification. 203×254 mm.

DETAILED DESCRIPTION

Figure 1C:
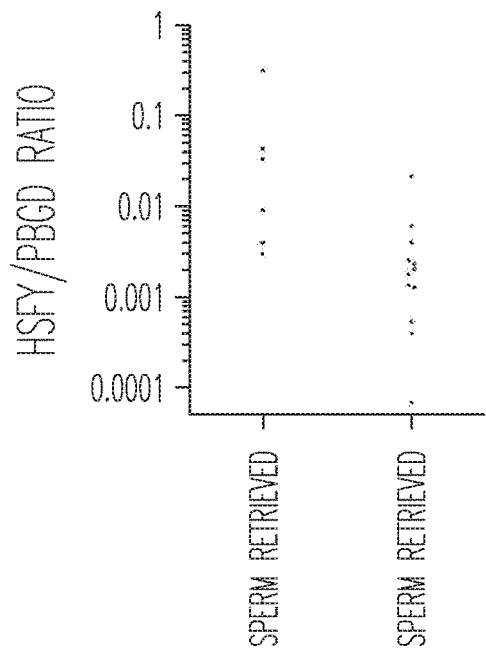

Testicular sperm extraction is a treatment commonly used for nonobstructive azoospermia (no sperm in the ejaculate). Unfortunately this procedure is very expensive, is usually not covered by insurance, often requires hormonal stimulation of the female partner, and subjects men to medical risk including testicular bleeding, infection, and postoperative testicular failure that may require lifelong hormonal replacement therapy with testosterone. Because of the significant financial costs and medical risks of testicular sperm extraction, there is a need for a test that can accurately identify the males where sperm will be retrieved and those where there is little hope of sperm retrieval. Currently such a test is not available, and surgical sperm retrieval fails in approximately 50% of cases.

The current invention solves this problem by providing methods for measurement of HSFY expression in test samples to predict the outcome of surgical sperm retrieval. As described herein, HSFY expression is a strong predictor of the outcome of successful testicular sperm extraction. It is a test that can be used preoperatively (alone or in combination with other clinical parameters) to greatly enhance the ability of medical personnel to predict the males in whom sperm are likely to be found. This is clinically helpful for counseling individual males about their odds for sperm retrieval, which aids their own decision making, and in identifying males in whom the costs and risks of sperm retrieval are not worthwhile.

Thus, in some embodiments, the invention relates to a method of evaluating whether to perform testicular sperm extraction in a male. The method involves quantifying HSFY expression in a fluid or tissue sample from the male to provide a quantified HSFY expression level for the male. The male's quantified HSFY expression level can be compared to baseline quantified HSFY expression levels obtained from men where sperm retrieval failed. If the male's quantified HSFY expression level is higher than the baseline quantified HSFY expression level, sperm can be retrieved from the male.

The benefits of HSFY testing are illustrated by considering the case of a male with idiopathic nonobstructive azoospermia (NOA) whose diagnostic biopsy shows Sertoli Cell only (SCO) histological pattern. In the absence of HSFY testing, physicians would counsel this patient that his chance of successful sperm retrieval as about 35-40% (Ramasamy & Schlegel, J. Urol. 177: 1447-49 (2007)). Nearly all such men elect to proceed with microdissection testicular sperm extraction (TESE) given the reasonably high chance of success. However, if such a patient tested positive for HSFY expression, he could be counseled that the chance of sperm retrieval is close to 100%. Conversely, if he were to test negative then the estimated chance of sperm retrieval would be 7%. Thus, while some men may still elect to proceed with microdissection testicular sperm extraction, the risks and expenses of unnecessary surgical procedures would be reduced by use of the HSFY screening method.

Heat Shock Transcription Factor, Y Chromosome (HSFY)

HSFY is a gene within the azoospermic factor (AZF) region of the Y chromosome (Yq11). HSFY encodes three different testis-specific transcripts that are thought to function by regulating expression of heat shock proteins. The HSFY transcripts and proteins are predominantly expressed in human testis, both in Sertoli cells and germ cells (Tessari et al., Molecular Human Reproduction; 10: 253-258 (2004)).

Sequences for various HSFY proteins and genes are available from the National Center for Biotechnology Information (NCBI) database (see, e.g., the website at ncbi.nlm.nih.gov). For example, an amino acid sequence for the heat shock transcription factor, Y-linked isoform 1 (*Homo sapiens*, chromosome location Yq11.222) is available as accession number NP_714927.1 (GI:32526913), and is reproduced below as SEQ ID NO:1.

```
  1  MAHVSSETQD VSPKDELTAS EASTRSPLCE HTFPGDSDLR

41  SMIEEHAFQV LSQGSLLESP SYTVCVSEPD KDDDFLSLNF

81  PRKLWKIVES DQFKSISWDE NGTCIVINEE LFKKEILETK

121  APYRIFQTDA IKSFVRQLNL YGFSKIQQNF QRSAFLATFL

161  SEEKESSVLS KLKFYYNPNF KRGYPQLLVR VKRRIGVKNA

201  SPISTLFNED FNKKHFRAGA NMENHNSALA AEASEESLFS

241  ASKNLNMPLT RESSVRQIIA NSSVPIRSGF PPPSPSTSVG

281  PSEQIATDQH AILNQLTTIH MHSHSTYMQA RGHIVNFITT

321  TTSQYHIISP LQNGYFGLTV EPSAVPTRYP LVSVNEAPYR

361  NMLPAGNPWL QMPTIADRSA APHSRLALQP SPLDKYHPNY

401  N
```

A nucleic acid encoding this SEQ ID NO:1 protein is available in the NCBI database as accession number NM_153716.1 (GI:32526912), and is reproduced below as SEQ ID NO:2.

```
  1 AACCATTGTG ATGGTCTAGA TAAGTGTACA TGCTTAGGCC
 41 TTCTGAAGCA GCATTTGAAG CTGCAGTCCT GAAAACCATG
 81 CAGGCCGGAA GAGTAGATAA AGAAATATTT ATTTGAGATG
121 GCACATGTTT CTTCAGAAAC TCAAGATGTT TCCCCCAAAG
161 ATGAATTAAC TGCTTCAGAA GCCTCCACTA GGTCTCCATT
201 GTGTGAACAC ACCTTCCCTG GGGACTCAGA CTTACGGTCA
241 ATGATTGAAG AACATGCTTT TCAGGTTTTG TCACAAGGAT
281 CCTTGTTAGA AAGTCCAAGT TACACAGTTT GTGTCTCTGA
321 GCCAGATAAA GATGATGATT TTCTTTCTCT GAACTTTCCC
361 AGGAAACTTT GGAAATAGT GGAAAGTGAC CAATTCAAGT
401 CTATTTCATG GGATGAGAAT GGAACTTGCA TAGTGATTAA
441 TGAAGAACTC TTCAAGAAAG AAATTTTGGA AACAAAGGCT
481 CCTTACAGAA TATTTCAAAC TGATGCTATC AAAAGTTTTG
521 TTCGACAGCT CAACCTTTAT GGATTTAGTA AAATTCAACA
561 GAATTTTCAA AGATCTGCCT TTCTAGCCAC CTTTCTGTCA
601 GAAGAGAAAG AATCGTCTGT CTTAAGCAAG TTAAAGTTCT
641 ATTATAATCC AAATTTCAAG CGTGGCTATC CCCAACTTTT
681 AGTAAGAGTG AAGAGAAGAA TTGGTGTTAA AAATGCTTCA
721 CCTATATCTA CTTTATTCAA CGAAGATTTC AACAAGAAGC
761 ATTTTAGAGC AGGGGCTAAC ATGGAGAATC ATAATTCTGC
801 CTTAGCTGCT GAAGCTAGTG AAGAAAGTTT ATTTTCAGCC
841 TCTAAAAATT TAAATATGCC TCTAACAAGG GAATCTTCTG
881 TCAGACAGAT AATTGCAAAT TCATCTGTCC CCATTAGAAG
901 TGGTTTCCCT CCTCCTTCAC CTTCAACCTC AGTTGGACCA
961 TCAGAACAAA TTGCAACAGA TCAACATGCT ATTTTAAATC
1001 AGTTGACCAC TATTCATATG CACTCTCATA GTACCTACAT
1041 GCAAGCAAGG GGCCACATTG TGAATTTTAT TACAACCACA
1081 ACTTCTCAAT ACCACATCAT ATCTCCCTTA CAAAATGGTT
1121 ATTTTGGGCT GACAGTGGAA CCATCTGCTG TTCCCACACG
1161 ATATCCTCTG GTATCAGTCA ATGAGGCTCC ATATCGTAAC
1201 ATGCTACCAG CAGGCAACCC GTGGTTGCAA ATGCCTACGA
1241 TCGCTGATAG ATCAGCTGCC CCTCATTCCA GGCTAGCTCT
1281 TCAACCATCA CCACTGGACA AATATCACCC TAATTACAAC
1321 TGATCTGCCA TTAAAAGAGG ACCAGATTAT GAATGACAAC
1361 AGAGACTAAC ATTTACATTG ACAAAAAACC CTAAAAATTT
1401 CTGCAATTAT CTTATTGAAC AATAAAATTG CATGTTTACT
1441 TCT
```

Another amino acid sequence for a HSFY protein is the following sequence for heat shock transcription factor, Y-linked isoform 2 (Homo sapiens, chromosome location Yq11.222) is available as accession number NP_001001877.1 (GI:50312659). This sequence is reproduced below as SEQ ID NO:3.

```
  1 MAHVSSETQD VSPKDELTAS EASTRSPLCE HTFPGDSDLR
 41 SMIEEHAFQV LSQGSLLESP SYTVCVSEPD KDDDFLSLNF
 81 PRKLWKIVES DQFKSISWDE NGTCIVINEE LFKKEILETK
121 APYRIFQTDA IKSFVRQLNL YGFSKIQQNF QRSAFLATFL
161 SEEKESSVLS KIRFTKMKLS RSSTYENRYL CCNLHLKDES
201 NYS
```

A nucleic acid for the SEQ ID NO:3 HSFY protein is available in the NCBI database as accession number NM_001001877.1 (GI:50312658), and is reproduced below as SEQ ID NO:4.

```
  1 TAAGTGTACA TGCTTAGGCC TTCTGAAGCA GCATTTGAAG
 41 CTGCAGTCCT GAAAACCATG CAGGCCGGAA GAGTAGATAA
 81 AGAAATATTT ATTTGAGATG GCACATGTTT CTTCAGAAAC
121 TCAAGATGTT TCCCCCAAAG ATGAATTAAC TGCTTCAGAA
161 GCCTCCACTA GGTCTCCATT GTGTGAACAC ACCTTCCCTG
201 GGGACTCAGA CTTACGGTCA ATGATTGAAG AACATGCTTT
241 TCAGGTTTTG TCACAAGGAT CCTTGTTAGA AAGTCCAAGT
281 TACACAGTTT GTGTCTCTGA GCCAGATAAA GATGATGATT
321 TTCTTTCTCT GAACTTTCCC AGGAAACTTT GGAAAATAGT
361 GGAAAGTGAC CAATTCAAGT CTATTTCATG GGATGAGAAT
401 GGAACTTGCA TAGTGATTAA TGAAGAACTC TTCAAGAAAG
441 AAATTTTGGA AACAAAGGCT CCTTACAGAA TATTTCAAAC
481 TGATGCTATC AAAAGTTTTG TTCGACAGCT CAACCTTTAT
521 GGATTTAGTA AAATTCAACA GAATTTTCAA AGATCTGCCT
561 TTCTAGCCAC CTTTCTGTCA GAAGAGAAAG AATCGTCTGT
601 CTTAAGCAAG ATACGCTTCA CCAAAATGAA ACTTTCCAGA
641 TCTTCAACTT ATGAAAACAG GTATTTATGT TGCAACTTAC
681 ATTTAAAAGA TGAGTCGAAT TACTCATAAT CCTTAGAAGT
721 TAGCTTGTCC GCATCTGAAA ATTCACTTTT ACCTTGAAGT
761 TCAATCTGTC TCTGGGAAAG ACTAGATTGG AAGAATAAAA
801 TTCAAGAATG TGATGTTTTA GTAATGGAAA AGCCAAGAGC
841 GTCAGGTGGC AAAAGTCCTT CTGTTACTCA AGAAAATGCT
881 CTGAAAAATT CCTTTTCTCT TTTTTTTTTG TAAAGATTAA
921 CTCCACCTCA CCACCACAAT GAGGTATTTT TCTCAGCAAT
961 TGACACCTGT TTACTCAGTT ACTCCCTGTA ACTATGTTAT
1001 GCTGTGAAGT AGGCAATACA GTTGTTAAAG AAGAATAA
```

Advances in molecular biological techniques and improvements in the understanding of spermatogenesis enable new diagnostic approaches in males with nonobstructive azoospermia. One approach that has been used previously with some success is detection of spermatogenesis-specific mRNAs in testis tissue by quantitative reverse transcription polymerase chain reaction (RT-PCR) (Kleiman et. al 2001, Song et. al. 2000). HSFY sequences can be used to design primers, probes and obtain antibodies useful for detecting HSFY expression levels. Such probes and primers can be complementary and/or homologous to selected HSFY RNA sequences.

As described herein, the levels of expression of the heat shock factor Y chromosome (HSFY) gene in testicular or semen samples is a surprisingly effective marker for assessing whether sperm can be obtained from men with any of the histological variants of nonobstructive azoospermia, particularly those with Sertoli Cell only (SCO) histology.

For example, as shown herein, higher HSFY expression is higher in patients when sperm are retrieved than in patients where sperm were not successfully retrieved. Thus, HSFY/PBGD expression ratios determined with qRT-PCR were significantly higher when sperm were retrieved from patients ($7.76 \times 10^{-2} \pm 2.47 \times 10^{-2}$) than when sperm were not retrieved from patients ($1.9 \times 10^{-3} \pm 8.0 \times 10^{-4}$, $p<0.0001$). In the Sertoli Cell Only (SCO) subgroup HSFY/PBGD expression ratios were also significantly higher when sperm were retrieved ($5.70 \times 10^{-2} \pm 1.5 \times 10^{-3}$) compared to SCO subgroup HSFY/PBGD expression ratios where sperm were not retrieved ($6.00 \times 10^{-4}$, $p<0.0001$). Similarly, in the maturation arrest (MA) subgroup HSFY/PBGD expression ratios were also significantly higher when sperm were retrieved ($6.52 \times 10^{-2} \pm 4.76 \times 10^{-2}$) compared to MA subgroup HSFY/PBGD expression ratios where sperm were not retrieved ($3.6 \times 10^{-1} \pm 1.6 \times 10^{-1}$, $p=0.0076$). Comparison was not performed in the hypospermatogenesis subgroup because sperm were retrieved in all cases. The areas under the ROC curves derived from the qRT-PCR data for the overall study population and for the SCO and MA subgroups were 0.89, 0.98, and 0.90, respectively. Sensitivity and specificity were 67% and 93% for the overall study population, 92% and 100% for the SCO subgroup, and 67% and 92% for the MA subgroup. The estimated probabilities of sperm retrieval for HSFY positive males were 93% overall, 100% for males with SCO histology, and 91% for males with MA. The estimated probabilities of retrieval for HSFY negative males were 31% overall, 7% for SCO males, and 32% for males with MA histology. FISH results were consistent with the qRT-PCR data. We observed high expression of HSFY mRNA in testicular tissue derived from males with NOA. In contrast, expression was markedly decreased in testicular tissue derived from males with NOA who failed microdissection TESE.

Thus, the heat shock factor Y chromosome (HSFY) is a useful marker for determining whether sperm can successfully be obtained from males.

mRNA Detection and/or Quantification

Any method known to those in the art can be employed for determining the level of gene expression. Non-limiting examples of such techniques include microarray analysis, Northern blotting, nuclease protection assays, RNA fingerprinting, polymerase chain reaction, ligase chain reaction, Qbeta replicase, isothermal amplification method, strand displacement amplification, transcription based amplification systems, quantitative nucleic acid amplification assays (e.g., polymerase chain reaction assays), combined reverse transcription/nucleic acid amplification, nuclease protection (S1 nuclease or RNAse protection assays), Serial Analysis Gene Expression (SAGE) as well as other methods.

In general, the HSFY expression levels are provided as a ratio of the amount of RNA detected for HSFY relative to a housekeeping gene (e.g., porphobilinogen-deaminase (PBGD)) to normalize for variations that may inadvertently be introduced during tissue isolation, RNA purification, etc. Housekeeping genes that may be used for this purpose include, for example, ubiquitin C, beta-actin, GAPDH, 18S ribosomal RNA (18S rRNA) and porphobilinogen-deaminase (PBGD).

In some embodiments, an mRNA of HSFY is detected from a cell sample from a nonobstructive azoospermia man. Any method known to those in the art can be employed for determining the level of mRNA of HSFY. Typically, total RNA, which includes mRNA, is isolated. RNA can be isolated from the sample by any method known to those in the art. For example, commercial kits, such as the TRI Reagent® commercially available from Molecular Research Center, Inc. (Cincinnati, Ohio), can be used to isolate RNA.

The quantification of mRNA of HSFY from total mRNA from the sample can be performed by any method known to those in the art. For example, kinetic, quantitative PCR can be employed that involves reverse transcribing mRNA of HSFY by using reverse-transcriptase polymerase chain reaction (RT-PCR) to obtain HSFY cDNA. The cDNA can then, for example, be amplified by PCR followed by quantification using a suitable detection apparatus. See Example 2 below for a description of the quantification of mRNA of HSFY by kinetic, quantitative PCR.

For example, the isolated mRNA of HSFY may be amplified by methods known in the art. Amplification systems utilizing, for example, PCR or RT-PCR methodologies are known to those skilled in the art. For a general overview of amplification technology, see, for example, Dieffenbach et al., PCR Primer: A Laboratory Manual, Cold Spring Harbor Laboratory Press, New York (1995). For example, levels of mRNA of HSFY can be determined using kinetic, quantitative PCR.

An alternative method for determining the level of mRNA of HSFY includes the use of molecular beacons and other labeled probes useful in, for example multiplex PCR. In a multiplex PCR assay, the PCR mixture contains primers and probes directed to the HSFY PCR product. For example, a single fluorophore can be used in the assay. The molecular beacon or probe is detected to determine the level of mRNA of HSFY. Molecular beacons are described, for example, by Tyagi and Kramer (Nature Biotechnology 14, 303-308, 1996) and by Andrus and Nichols in U.S. Patent Application Publication No. 20040053284.

Another method includes, for instance, quantifying cDNA (obtained by reverse transcribing the mRNA of HSFY using a fluorescence based real-time detection method, such as the ABI PRISM 7500, 7700, or 7900 Sequence Detection System (TaqMan®) commercially available from Applied Biosystems, Foster City, Calif. or similar system as described by Heid et al., (Genome Res. 1996; 6:986-994) and Gibson et al. (Genome Res. 1996; 6:995-1001).

Primers useful for detecting HSFY expression levels can be complementary or homologous to specific HSFY nucleic acid sequences, for example, any of HSFY nucleic acids with SEQ ID NOs: 2 or 4, Such primers can be of varying lengths. For example, primers useful for detecting HSFY expression levels can be at least 12, at least 13, at least 14, at least 15, or at least 16, at least 17, at least 18, at least 19, at least 20, at least 21, at least 22, at least 23, or at least 24 consecutive nucleotides in length. In some embodiments, the primers are about 14, about 15, about 16, about 17, about 18, about 19, about 20, about 21, about 22, about 23, about 24, about 25, about 26, or about 27 consecutive nucleotides in length.

In some embodiments, a microarray can be used. Microarrays are known in the art and consist of a surface to which probes that correspond in sequence to gene products (e.g. mRNAs, polypeptides, fragments thereof etc.) can be specifically hybridized or bound to a known position. Hybridization intensity data can be detected by a scanner and the data automatically acquired and processed, for example, by an Affymetrix Microarray Suite (MAS5) software. Raw data can be normalized to expression levels using a set target intensity (e.g., 150). An alternate method to measure gene expression profiles of HSFY, baseline and control genes is, for example, by classical TaqMan® Gene Expression Assays or TaqMan® Low Density Array—micro fluidic cards (Applied Biosystems). Here, quantitative data are obtained by real-time RT-PCR in a small reaction volume.

The transcriptional state of a cell may be measured by other gene expression technologies known in the art. Several such technologies produce pools of restriction fragments of limited complexity for electrophoretic analysis, such as methods combining double restriction enzyme digestion with phasing primers (e.g. EP-A1-0 534858), or methods selecting restriction fragments with sites closest to a defined mRNA end (e.g. Prashar et al; Proc. Nat. Acad. Sci., 93, 659-663, 1996). Other methods statistically sample cDNA pools, such as by sequencing sufficient bases (e.g. 20-50 bases) in each multiple cDNAs to identify each cDNA, or by sequencing short tags (e.g. 9-10 bases) which are generated at known positions relative to a defined mRNA end (e.g. Velculescu, Science, 270, 484-487, 1995) pathway pattern.

Nuclease protection assays such as ribonuclease protection assays and S1 nuclease assays, can be used to detect and quantify specific HSFY. In nuclease protection assays, an antisense probe (labeled with, e.g., radiolabeled or nonisotopic) hybridizes in solution to an RNA sample. Following hybridization, single-stranded, unhybridized probe and RNA are degraded by nucleases. An acrylamide gel is used to separate the remaining protected fragments. Typically, solution hybridization is more efficient than membrane-based hybridization, and it can accommodate up to 100 μg of sample RNA, compared with the 20-30 μg maximum of blot hybridizations.

A ribonuclease protection assay employs RNA probes. Oligonucleotides and other single-stranded DNA probes can only be used in assays containing S1 nuclease. The single-stranded, antisense probe must typically be completely homologous to target RNA to prevent cleavage of the probe:target hybrid by nuclease.

Serial Analysis Gene Expression (SAGE), which is described in e.g., Velculescu et al., 1995, *Science* 270:484-7; Carulli, et al., 1998, *Journal of Cellular Biochemistry Supplements* 30/31:286-96, can also be used to determine RNA abundances in a cell sample.

In other embodiments, a standard Northern blot assay can be used to ascertain the relative amounts of mRNA in a sample, in accordance with conventional Northern hybridization techniques known to those persons of ordinary skill in the art. In Northern blots, RNA samples are first separated by size via electrophoresis in an agarose gel under denaturing conditions. The RNA is then transferred to a membrane, crosslinked and hybridized with a labeled probe. Nonisotopic or high specific activity radiolabeled probes can be used including random-primed, nick-translated, or PCR-generated DNA probes, in vitro transcribed RNA probes, and oligonucleotides. Additionally, sequences with only partial homology (e.g., a HSFY from a different species or genomic DNA fragments that might contain an exon) may be used as probes.

The labeled probe for assay of RNA expression levels can be a radio-labeled cDNA; a full-length, single stranded labeled RNA or DNA, or a labeled fragment of that RNA or DNA sequence. Such a RNA or DNA a probe can be single-stranded or partially single-stranded. The probe(s) can be of variable length, for example, with at least 12, at least 13, at least 14, at least 15, or at least 16, at least 17, at least 18, at least 19, at least 20, at least 21, at least 22, at least 23, or at least 24 consecutive nucleotides. In some embodiments, the probe is about 12, about 13, about 14, about 15, about 16, about 17, about 18, about 19, about 20, about 21, about 22, about 23, about 24, or about 25 consecutive nucleotides in length. In further embodiments, the probe may be at least 20, at least 30, at least 50, or at least 70 consecutive nucleotides in length. The probe can be less than 50, less than 45, or less than 40 consecutive nucleotides in length. The probe can be labeled by any of the many different methods known to those skilled in this art.

The labels or reporter molecules commonly employed for nucleic acid probes or for labeling antibodies and other binding entities are radioactive elements, enzymes, chemicals that fluoresce when exposed to ultraviolet light, and others. A number of fluorescent materials are known and can be utilized as labels. These include, but are not limited to, fluorescein, rhodamine, auramine, Texas Red, AMCA blue and Lucifer Yellow. The radioactive label can be detected by any of the currently available counting procedures. Non-limiting examples of isotopes include $^{3}H$, $^{14}C$, $^{32}P$, $^{35}S$, $^{36}Ci$, $^{51}Cr$, $^{57}Co$, $^{58}Co$, $^{59}Fe$, $^{90}Y$, $^{125}I$, $^{131}I$, and $^{186}Re$. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Any enzymes known to one of skill in the art can be utilized. Examples of such enzymes include, but are not limited to, peroxidase, beta-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

Generally, the level of HSFY in a test sample is upregulated if the gene expression of HSFY is increased relative to HSFY expression levels in similar samples from men where sperm retrieval was unsuccessful (e.g., a baseline). For example, the baseline can be HSFY expression levels in tissue or fluid samples from men with nonobstructive azoospermia and failed sperm retrieval from their testes. In some embodiments, up-regulation includes increases HSFY expression above baseline level by 10%, 15%, 20%, 25%, 30%, 35%, 40%, 45%, 50%, 55%, 60%, 65%, 70%, 75%, 80%, 85%, 90%, 95%, 100%, 150% or higher. In some embodiments, upregulation includes increases HSFY expression two-fold, three-fold, four-fold, five-fold, six-fold, seven-fold, eight-fold, nine-fold, ten-fold or more above baseline HSFY expression levels.

In some embodiments, a discriminatory level for upregulated gene expression of HSFY is employed to allow assessment of whether the test sample has HSFY expression levels indicating sperm can be retrieved from the testes of the male. For example, such a discriminatory level for upregulated gene expression can be a baseline magnitude of HSFY gene expression. In some embodiments, such a discriminatory level for upregulated gene expression is the mean±95% confidence interval of a group of values observed in males where sperm retrieval was not successful. In other embodiments, such a discriminatory level for upregulated gene expression is the mean±95% confidence interval of a group of values observed in males with nonobstructive azoospermia and with AZFb microdeletions (e.g., baseline levels).

Upregulation of gene expression of HSFY in a sample is considered to be significantly greater if the quantified HSFY expression value in the sample is greater than the mean±95% confidence interval of a group of values observed in nonobstructive azoospermia men with AZFb microdeletions. Similarly, the level of HSFY in the cell sample is considered to be significantly lower if the HSFY value is lower than the mean±95% confidence interval of a group of values observed in nonobstructive azoospermia men with AZFb microdeletions.

In some embodiments, for interpretation of quantitative gene expression measurements, a normalizer may be needed to correct expression data for differences in cellular input, RNA quality, and RT efficiency between samples. In some embodiments, PBGD rRNA is used for normalization in gene expression analysis.

A baseline sample is typically the level of HSFY from nonobstructive azoospermia (NOA) men failing sperm retrieval or NOA men with AZFb microdeletions. It will be understood by those of ordinary skill in the art that it is not necessary to determine the level of HSFY in a baseline sample every time the method is conducted. For example, the HSFY levels in the testicular tissue or semen cell sample from the nonobstructive azoospermia man can be compared to that of one or more previously determined baseline samples or to a level recognized by the physician or clinician conducting the method of a consensus of medical and/or clinical practitioners.

In some embodiments, there is provided a method for detecting successful sperm retrieval where levels of gene expression are compared to a baseline level of gene expression, which is performed using log-transformed mRNA levels in the cell sample and comparing it with log-transformed mRNA levels of HSFY of a baseline sample from a nonobstructive azoospermia subject failing sperm retrieval. If there is upregulation of mRNA levels of HSFY from the cell sample relative to the baseline level of gene expression in the baseline sample, this indicates successful sperm retrieval.

Proteins

In some embodiments, the HSFY expression levels are measured by determining the amount of HSFY protein expressed. Detection of elevated or decreased protein levels may be used to predict the ability or inability to retrieve sperm from a male.

In some embodiments, protein levels are detected in a selected fluid or tissue sample (e.g., testicular tissue, blood, urine, semen). Any available methods for detecting proteins can be employed. Examples of such methods include Western blotting, enzyme-linked immunosorbent assays (ELISAs), radioimmunoassay, immunocytochemistry, immunohistochemistry, flow cytometry, immunoprecipitation, one- and two-dimensional electrophoresis, mass spectroscopy and detection of enzymatic activity.

Antibodies and other binding entities can be used to detect expression levels of HSFY proteins. Such antibodies and binding entities can be prepared by available methods. For example, available HSFY amino acid sequences, including those illustrated herein, can be used to make HSFY antibodies and binding entities. Suitable antibodies may include polyclonal, monoclonal, fragments (such as Fab fragments), single chain antibodies and other forms of specific binding molecules. Briefly, these protein detection assays can include contacting a test sample with an antibody specific to the protein, detecting the presence of a complex between the antibody and the protein. In some embodiments, a signal from the protein-antibody complex is detected.

Such antibody-based detection methods can include quantifying the amount of HSFY expression, for example, by detecting the amount of signal from a labeled HSFY-antibody complex. A variety of immuno-detection methods can be employed for this purpose, including, but not limited to, Western Blot, ELISA, radioimmunoassay, immunocytochemistry, immunohistochemistry, flow cytometry, and immunoprecipitation.

Anti-HSFY antibodies may also be used to determine the presence or quantity of HSFY protein in a sample. Generally speaking, such antibodies can be employed in any type of immunoassay, whether qualitative or quantitative. This includes both the two-site sandwich assay and the single site immunoassay of the non-competitive type, as well as in traditional competitive binding assays.

One embodiment of interest, for ease of detection, and its quantitative nature, is the sandwich or double antibody assay, of which a number of variations exist, all of which are intended to be encompassed by this portion of the present invention. For example, in a typical forward sandwich assay, unlabeled antibody is immobilized on a solid substrate, e.g., within microtiter plate wells, and the sample to be tested is brought into contact with the bound molecule. After a suitable period of incubation, for a period of time sufficient to allow formation of an antibody-antigen binary complex, a second antibody, labeled with a reporter molecule capable of emitting or inducing a detectable signal, is then added and incubation is continued allowing sufficient time for binding with the antigen at a different site and the formation of a ternary complex of antibody-antigen-labeled antibody. Any unreacted material is washed away, and the presence of the antigen is determined by observation of a signal, which may be quantified by comparison with a control or baseline sample containing known amounts of antigen.

Variations on the forward sandwich assay include the simultaneous assay, in which both sample and antibody are added simultaneously to the bound antibody, or a reverse sandwich assay in which the labeled antibody and sample to be tested are first combined, incubated and added to the unlabelled surface bound antibody. These techniques are well known to those skilled in the art, and the possibility of minor variations will be readily apparent. As used herein, "sandwich assay" is intended to encompass all variations on the basic two-site technique.

For the sandwich assays, the only limiting factor is that both antibodies have different binding specificities for the HSFY epitopes. Thus, a number of possible combinations are possible. As a more specific example, in a typical forward sandwich assay, a primary antibody is either covalently or passively bound to a solid support. The solid surface is usually glass or a polymer, the most commonly used polymers being cellulose, polyacrylamide, nylon, polystyrene, polyvinylchloride or polypropylene. The solid supports may be in the form of tubes, beads, discs or microplates, or any other surfaces suitable for conducting an immunoassay.

Conventional antibody binding processes can be employed. Following binding, the solid phase-antibody complex is washed in preparation for the test sample. An aliquot of the test sample is then added to the solid phase complex and incubated at 25° C. for a period of time sufficient to allow binding of any HSFY proteins present to the anti-HSFY antibody. The second antibody is then added to the solid phase complex and incubated at 25° C. for an additional period of time sufficient to allow the second antibody to bind to the primary antibody-antigen solid phase complex. The second antibody may be linked to a reporter molecule, the visible signal of which is used to indicate the binding of the second antibody to any antigen in the sample.

As used herein, a "reporter molecule" is a molecule that provides an analytically detectable signal, allowing the detection of antigen-bound antibody. In some embodiments, detection is preferably at least relatively quantifiable, to allow determination of the amount of antigen in the sample, this may be calculated in absolute terms, or may be done in comparison with a standard (or series of standards) containing a known normal level of antigen.

Many commonly used reporter molecules in this type of assay are either enzymes or fluorophores. In the case of an enzyme immunoassay an enzyme is conjugated to the second antibody, often by means of glutaraldehyde or periodate. As will be readily recognized, however, a wide variety of different conjugation techniques exist, which are well known to the skilled artisan. Commonly used enzymes include horseradish peroxidase, glucose oxidase, beta-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product rather than the chromogenic substrates noted above. In all cases, the enzyme-labeled antibody is added to the first antibody-antigen complex and allowed to bind to the complex, and then the excess reagent is washed away. A solution containing the appropriate substrate is then added to the tertiary complex of antibody-antigen-labeled antibody. The substrate reacts with the enzyme linked to the second antibody, giving a qualitative visual signal, which may be further quantified, usually spectrophotometrically, to give an evaluation of the amount of antigen that is present in the serum sample.

Additionally, fluorescent compounds, such as fluorescein or rhodamine, may be chemically coupled to antibodies without altering their binding capacity. When activated by illumination with light of a particular wavelength, the fluorophore-labeled antibody absorbs the light energy, inducing a state of excitability in the molecule, followed by emission of the light at a characteristic longer wavelength. The emission appears as a characteristic color visually detectable with a light microscope. As in the enzyme immunoassay (EIA), the fluorescent-labeled antibody is allowed to bind to the first antibody-tagged protein complex. After washing the unbound reagent, the remaining ternary complex is then exposed to light of the appropriate wavelength, and the fluorescence observed indicates the presence of the antigen.

Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

In another embodiment, the sample to be tested may be used in a single site immunoassay wherein it is adhered to a solid substrate either covalently or non-covalently. An unlabeled anti-HSFY antibody is brought into contact with the sample bound on the solid substrate. After a suitable period of incubation, for a period of time sufficient to allow formation of an antibody-antigen binary complex a second antibody, labeled with a reporter molecule capable of inducing a detectable signal, is then added and incubation is continued allowing sufficient time for the formation of a ternary complex of antigen-antibody-labeled antibody. For the single site immunoassay, the second antibody may be a general antibody (i.e., zenogeneic antibody to immunoglobulin, particularly anti-(IgM and IgG) linked to a reporter molecule) that is capable of binding an antibody that is specific for the HSFY protein of interest.

Definitions

The term "biopsy" refers to a specimen obtained by removing tissue from a living male mammal for diagnostic examination. The term includes aspiration biopsies, brush biopsies, chorionic villus biopsies, endoscopic biopsies, excision biopsies, needle biopsies (specimens obtained by removal by aspiration through an appropriate needle or trocar that pierces the skin, or the external surface of an organ, and into the underlying tissue to be examined), open biopsies, punch biopsies (trephine), shave biopsies, sponge biopsies, and wedge biopsies. Biopsies also include a fine needle aspiration biopsy, a minicore needle biopsy, and/or a conventional percutaneous core needle biopsy.

The term "hybridization" includes a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under conditions of different "stringency". The stringency of a hybridization reaction includes the difficulty with which any two nucleic acid molecules will hybridize to one another. Under stringent conditions, nucleic acid molecules at least 60%, 65%, 70%, 75% identical to each other remain hybridized to each other, whereas molecules with low percent identity cannot remain hybridized. A preferred, non-limiting example of highly stringent hybridization conditions are hybridization in 6× sodium chloride/sodium citrate (SSC) at about 45° C., followed by one or more washes in 0.2×SSC, 0.1% SDS at 50° C., preferably at 55° C., more preferably at 60° C., and even more preferably at 65° C. When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to hydrogen bond with each other, according to generally accepted base-pairing rules.

A "gene" includes a polynucleotide containing at least one open reading frame that is capable of encoding a particular polypeptide or protein after being transcribed and translated. Any of the polynucleotide sequences described herein may be used to identify larger fragments or full-length coding sequences of the gene with which they are associated.

Methods of isolating larger fragment sequences are known to those of skill in the art, some of which are described herein.

A "gene product" or "gene expression" includes an amino acid (e.g., peptide or polypeptide) generated when a gene is transcribed and translated. In some embodiments, the target gene expresses proteins of heat shock factor Y chromosome (HSFY). The term "level of gene expression" as used herein refers to quantifying gene expression. In some embodiments, to accurately assess whether increased mRNA is significant, it is preferable to "normalize" gene expression to accurately compare levels of expression between samples, i.e., it is a baseline level against which gene expression is compared. Quantification of gene expression can be accomplished by methods known in the art, such as, for example, reverse transcription polymerase chain reaction (RT-PCR), TAQMAN® assays or the like. Gene expression can also be quantified by detecting the protein and/or peptide directly, in a variety of assay formats known to those of ordinary skill in the art, including but not limited to enzyme linked immunosorbent assay (ELISA), radioimmunoassay (RIA), immunofluorimetry, immunoprecipitation, equilibrium dialysis, immunodiffusion, immunoblotting, mass spectrometry and other techniques. See, e.g., Harlow and Lane, Antibodies: A Laboratory Manual, Cold Spring Harbor Laboratory, 1988; Weir, D. M., Handbook of Experimental Immunology, 1986, Blackwell Scientific, Boston.

As used herein, the term "biomarker" includes a polynucleotide or polypeptide molecule which is present or increased in quantity or activity in subjects having viable sperm to be retrieved.

As used herein, "obtaining a test sample" involves removing a sample of tissue or fluid from a male, receiving a sample of tissue or fluid from a male, receiving a male's tissue or fluid sample from a physician, receiving a male's tissue or fluid sample via mail delivery and/or removing a male's tissue or fluid sample from a storage apparatus or facility. Thus, obtaining a test sample can involve removal or receipt of the test sample directly from the male, but obtaining a test sample can also include receipt of a test sample indirectly from a medical worker, from a storage apparatus/facility, from a mail delivery service after transportation from a medical facility, and any combination thereof. Thus, the test sample can originate in one location, and be transported to another location where it is received and tested. Any of these activities or combinations of activities involves "obtaining a test sample."

As used herein, "obtaining a quantified expression level of HSFY" involves directly or indirectly assaying or physically manipulating a test sample to determine a concentration or an amount of HSFY mRNA in the test sample. A person can directly obtain a quantified expression level of HSFY, for example, by obtaining a test sample and subjecting the test sample to any available procedure for quantifying mRNA expression levels. A person can indirectly obtain a quantified expression level of HSFY, for example, by obtaining a test sample and requesting that another person subject the test sample to an available procedure for quantifying mRNA expression levels. The people involved in "obtaining a quantified expression level of HSFY" can be employed by the same entity or different entities. "Obtaining a quantified expression level of HSFY" can include partially or substantially purifying mRNA from the test sample. "Obtaining a quantified expression level of HSFY" can include addition of reagents, enzymes, diluents and/or other chemicals to the impure, partially pure or substantially pure mRNA in or from the test sample. "Obtaining a quantified expression level of HSFY" can also include use of a machine to evaluate or detect the amount or concentration of HSFY mRNA in the test sample. "Obtaining a quantified expression level of HSFY" can provide a HSFY quantified test result. Any of these activities or combinations of activities involves "obtaining a quantified expression level of HSFY."

A "probe or primer" as used herein refers to a group of nucleic acids that may be used to detect one or more genes (e.g. HSFY). Detection may be, for example, through amplification as in PCR and RT-PCR, or through hybridization, or through selective destruction and protection, as in assays based on the selective enzymatic degradation of single or double stranded nucleic acids, or by detecting mRNA. Probes and/or primers may be labeled with one or more fluorescent, radioactive, quenchers, or other detectable moieties (including enzymes). Probes may be any size so long as the probe is sufficiently large to selectively detect the desired gene or be amplified.

Primers can be polynucleotides or oligonucleotides capable of being extended in a primer extension reaction at their 3' end. In order for an oligonucleotide to serve as a primer, it typically needs only be sufficiently complementary in sequence to be capable of forming a double-stranded structure with the template, or target, under the conditions employed. Establishing such conditions typically involves selection of solvent and salt concentration, incubation temperatures, incubation times, assay reagents and stabilization factors known to those in the art. The term primer or primer oligonucleotide refers to an oligonucleotide as defined herein, which is capable of acting as a point of initiation of synthesis when employed under conditions in which synthesis of a primer extension product that is complementary to a nucleic acid strand is induced, as, for example, in a DNA replication reaction such as a PCR reaction. Like non-primer oligonucleotides, primer oligonucleotides may be labeled according to any technique known in the art, such as with radioactive atoms, fluorescent labels, enzymatic labels, proteins, haptens, antibodies, sequence tags, mass label or the like. Such labels may be employed by associating them, for example, with the 5' terminus of a primer by a plurality of techniques known in the art. Such labels may also act as capture moieties. A probe or primer may be in solution, as would be typical for multiplex PCR, or a probe or primer may be adhered to a solid surface, as in an array or microarray. It is well known that compounds such as PNAs may be used instead of nucleic acids to hybridize to genes. In addition, probes may contain rare or unnatural nucleic acids such as inosine.

The term "up-regulation" or "up-regulated" are used interchangeably herein and refer to the increase or elevation in the amount of a target gene or a target protein. The term "up-regulation" or "up-regulated" also refers to the increase or elevation of processes or signal transduction cascades involving a target gene or a target protein. In some embodiments, upregulation includes increases above a baseline level of 10%, 15%, 20%, 25%, 30%, 35%, 40%, 45%, 50%, 55%, 60%, 65%, 70%, 75%, 80%, 85%, 90%, 95%, 100% or higher.

Kits

Another aspect of the invention includes kits for detecting and quantifying HSFY expression levels in test samples. The kits can include any reagents, components and instructions useful for testing, assaying and/or determining HSFY expression levels in samples. The kits can include reagents, components and instructions for detecting and/or quantifying HSFY RNA or protein levels. For example, the kits may include primers, probes, enzymes and/or other components for quantifying HSFY mRNA levels in a sample. In other embodiments, the kits may include anti-HSFY antibodies, and a detection means for detecting an HSFY-antibody complex (e.g., a label or reporter molecule that is either bound to the antibody or is capable of binding to the antibody or HSFY).

For example, one type of kit for detecting and/or quantifying HSFY mRNA expression levels may include a reverse transcriptase enzyme; a reverse transcriptase primer; a forward amplification primer; a reverse amplification primer; an amplification enzyme; one or more buffer solutions for performing reverse transcription and/or nucleic acid amplification; instructions for detecting and/or quantifying HSFY mRNA expression levels; or any combination thereof. The forward and reverse primers can have sequences complementary to HSFY (e.g., HSFY mRNA and/or cDNA). The kit may also include a control and/or a means for detecting and/or quantifying expression levels of a control gene (for example, a housekeeping gene). In one exemplary embodiment, the control may be a vector comprising a DNA sequence that encodes a known cDNA or nucleic acid.

The kit can include instructions for performing the methods described herein, for evaluating quantified HSFY mRNA expression levels, and/or for assessing the likelihood that sperm retrieval will be successful.

In the description provided herein, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

EXAMPLES

The present description is further illustrated by the following examples, which should not be construed as limiting in any way. The contents of all cited references (including literature references, issued patents, and published patent applications as cited throughout this application) are hereby expressly incorporated by reference.

Example 1: Patient Selection, Sample Acquisition and Handling Procedures

Patients.

The Institutional Review Board of the Weill Cornell Medical College approved this study. The study population was comprised of 54 men with nonobstructive azoospermia who underwent microdissection TESE. Nine men with azoospermia who underwent testicular sperm extraction served as controls. Patients were selected based upon availability of well-preserved testicular biopsies for pathologic analysis and availability of testicular tissue for research. Preoperative clinical evaluation included history, focused physical examination including measurement of testis size with an orchidometer, semen analysis, serum FSH level, karyotype analysis, and Y chromosome microdeletion testing.

Sperm Retrieval.

Azoospermia was confirmed on the day of planned sperm retrieval by microscopic analysis of ejaculated semen after centrifugation. Bilateral microdissection Micro dissection TESE was performed as has previously been described utilizing the operating microscope and one transverse incision in the tunica albuginea until sperm were found or the entire volume of testicular tissue was dissected (Schlegel 1999). Extracted testicular tissue from each dissected region of the testis was immediately placed into a small volume of fluid and mechanically disrupted with sharp scissors and sequential passes through a 22 gauge angiocatheter. A small aliquot (~1%) of the testis tissue suspension was then placed on a slide and cytologically examined in the operating room for the presence of sperm by an experienced andrologist in the operating room to direct the extent and duration of surgery. This slide was discarded after analysis. The remainder of each testis tissue suspension was subsequently analyzed in the andrology laboratory for identification of sperm. Microdissection TESE was considered successful if one or more sperm were found that were considered morphologically acceptable for ICSI.

Tissue Acquisition for Pathologic Analysis and Research.

Diagnostic testicular biopsies and seminiferous tubular tissue for research were taken during microdissection TESE after the tunica albuginea was widely opened. Randomly selected pieces of undisturbed seminiferous tubular tissue measuring 5-10 mm in greatest dimension were sharply excised with a curved Iris scissor. One piece of tissue was placed gently into Bouin's solution for pathological analysis. Another piece of excised tissue was placed without media into a cryovial, immediately snap frozen in liquid nitrogen vapor, and stored in our tissue bank at −80 C. In four cases additional tissue was immediately placed in Tissue-Tek O.C.T. embedding medium (Sakura Finetek, Calif., USA), snap frozen by submersion in 2-methylbutane cooled with dry ice, and stored at −80 C.

Pathologic Analysis of Diagnostic Testis Biopsies.

Histopathological analysis of the diagnostic biopsies was performed together with a genitourinary pathologist. Sections were stained with hematoxalin and eosin and examined with a light microscope under 100-400× magnification. Biopsies were classified according to the most advanced pattern of spermatogenesis observed anywhere within all sections analyzed. Biopsy samples were classified as Sertoli cell only (SCO) when germ cells were completely absent; as maturation arrest (MA) when germ cells were identified but mature, elongated spermatids were completely absent; and as HS when rare mature sperm were identified.

Example 2: Quantitative Analysis of HSFY mRNA Expression

Frozen seminiferous tubular tissue for RNA extraction was thawed and weighed. Tissue was homogenized using a Polytron PT-10/35 Homogenizer (Kinematica Inc, Lucerne, Switzerland). Total RNA was extracted in one step with Trizol LS Reagent (Invitrogen Corp., Carlsbad, Calif., USA) according to manufacturer specifications. To remove any contamination with genomic DNA, extracted RNA was incubated with RNase-free DNase for 30 minutes (Qiagen Inc., Hilden, Germany) and purified using a commercially available RNA-binding spin column (RNeasy Mini Kit, Qiagen Inc., Hilden, Germany) according to manufacturer instructions. RNA concentration was measured spectrophotometrically at 260 nm with the Life Science UV/Vis DU 530 spectrophotometer (Beckman Coulter, Inc., California, USA). RNA purity was confirmed by measurement of the A260/A280 ratio. cDNA was synthesized from 1 microgram of purified total RNA with random hexamer primers using the Transcriptor First Strand cDNA Synthesis Kit (Roche Diagnostics Corp., Basel, Switzerland) according to manufacturer specifications. Reactions were performed in the Applied Biosystems 2720 Thermal Cycler (Foster City, Calif., USA). cDNA was stored at −20 C until use.

HSFY transcript variant 1 mRNA level was measured using dual-color, multiplex quantitative real-time PCR (qRT-PCR) with the Universal Probe Library (UPL) hydrolysis probe set on a Light Cycler 480 instrument (Roche Diagnostics Corp., Basel, Switzerland). Porphobilinogen Deaminase (PBGD) was selected as the housekeeping gene for relative quantification based upon observations in the inventors' laboratory of consistent PBGD expression in human testis irrespective of histology (data not shown). The multiplex assay was designed using the UPL Assay Design Center provided by the UPL suppliers (http://www.roche-applied-science.com/sis/rtpcr/upl/adc.jsp). The forward and reverse primers 5'-GTCAATGAGGCTCCATATCGT-3' (SEQ ID NO: 5) and 5'-GATCGTAGGCATTTGCAACC-3' (SEQ ID NO: 6) were used in combination with UPL Probe #40 to detect HSFY transcript variant 1 mRNA. PBGD mRNA was detected with a proprietary Human PBGD Gene Assay (Roche Diagnostics Corp., Basel, Switzerland).

The inventors ran all qRT-PCR reactions in duplicate on 96-well plates. The 20 ul reaction mixture contained 5 uL of 1:5 diluted cDNA and 200 nM UPL probe, 200 nM PBGD probe, 200 nM forward and reverse primers for HSFY, 500 nM forward and reverse primers for PBGD, and 1× Lightcycler 480 Probes Master mix. The cycle protocol was as follows: denaturation at 95 C for 10 minutes, 45 cycles of 95 C for 10 seconds and 60 C for 30 seconds, and a cooling cycle to 55 C. HSFY/PBGD expression ratio was determined with Lightcycler 480 Relative Quantification software (Roche Diagnostics Corp., Basel, Switzerland). Standard curves were generated during each PCR run for both HSFY and PBGD by running the multiplex reaction in triplicate with serially diluted cDNA from a patient with OA. Crossing points were determined automatically by the second derivative maximum method. PCR-efficiency corrections were applied by the software based on the standard curves and the calculated efficiencies for the HSFY (1.7) and PBGD (1.6) reactions. The assay validity was confirmed by analysis of the HSFY/PBGD expression ratio in testicular tissue from a patient with an AZFb deletion that included loss of both copies of HSFY. The HSFY/PBGD expression ratio in this patient was negligible ($4.5 \times 10^{-5}$).

RESULTS: HSFY/PBGD expression ratios determined with qRT-PCR were significantly higher when sperm were retrieved in the overall study population ($7.76 \times 10^{-2} \pm 2.47 \times 10^{-2}$ vs. $1.9 \times 10^{-3} \pm 8.0 \times 10^{-4}$, p<0.0001), in the Sertoli Cell Only (SCO) subgroup ($5.70 \times 10^{-2} \pm 1.5 \times 10^{-3}$ vs. $6.00 \times 10^{-4}$, p<0.0001), and in the maturation arrest (MA) subgroup ($6.52 \times 10^{-2} \pm 4.76 \times 10^{-2}$ vs. $3.6 \times 10^{-3} \pm 1.6 \times 10^{-3}$, p=0.0076). Comparison was not performed in the hypospermatogenesis subgroup because sperm were retrieved in all cases.

Example 3: Fluorescent In Situ Hybridization (FISH)

Validation of the qRT-PCR assay was performed with FISH using testicular tissue from two patients with azoospermia and two nonobstructive azoospermia patients with Sertoli cell only histology who failed microdissection TESE. Frozen embedded testis tissue was cryosectioned at 5 micrometer thickness and placed on a glass slide. Slides were fixed with 4% buffered paraformaldehyde and permeabilized with 0.05% pepsin/10 mM HCl solution. Sections were post-fixed in 1% paraformaldehyde, dehydrated with a sequential series of ethanol washes, incubated in 70% formamide/2×SSC buffer solution, and dehydrated again with ethanol. Hybridization was performed using a labeled DNA probe that we synthesized. Forward and reverse primers were designed with the National Center for Biotechnology Information (NCBI) blast primer design program (see website at www.ncbi.nlm.nih.gov/tools/primer-blast/) for amplification of a 426 bp fragment of HSFY mRNA (forward primer 5'-TCAGAAGCCTCCACTAGGTCTCCA-3' [SEQ ID NO: 7], reverse primer 5'-TGACAGAAAGGTGGCTA-GAAAGGCA-3'[SEQ ID NO: 8]). The sequence was amplified by PCR using cDNA from a patient with azoospermia as a template and Faststart High Fidelity Polymerase (Roche Molecular Diagnostics, Pleasanton, Calif., USA) according to manufacturer specifications. The size of the amplified product was confirmed with gel electrophoresis. One microgram of PCR product was labeled with Alexa Fluor 488 using the Ulysis Nucleic Acid Labeling Kit (Invitrogen Corp., Carlsbad, Calif., USA) according to manufacturer specifications. The DNA probe was purified from excess labeling reagent using the Micro Bio-Spin Chromatography Column (Bio-Rad Laboratories, Hercules, Calif., USA). Labeled DNA probe at a final concentration of 10 ng/uL was added to hybridization buffer containing 65% formamide, denatured for 5 min at 72 C, and applied to the slide. Hybridization was performed overnight in a dark humidified chamber at 37 C. Slides were washed with 0.4×SSC buffer/ 0.3% NP-40 for 2 minutes at 37 C and with 2×SSC buffer/ 0.1% NP-40 for 1 minute at room temperature. Nuclear counterstaining was performed by application of ProLong Gold antifade reagent with DAPI (Invitrogen Corp., Carlsbad, Calif., USA). Fluorescent microscopy was performed using an upright Nikon Eclipse 50i fluorescent microscope equipped with Nikon UV-2A and Semrock Brightline GFP-3035B fluorescence filters and NIS-Elements Basic research software (Nikon, N.Y., USA). Images were acquired with 600 millisecond exposure times at 100× magnification using a Nikon Digital Sight—QiIMc camera.

Figure 3:
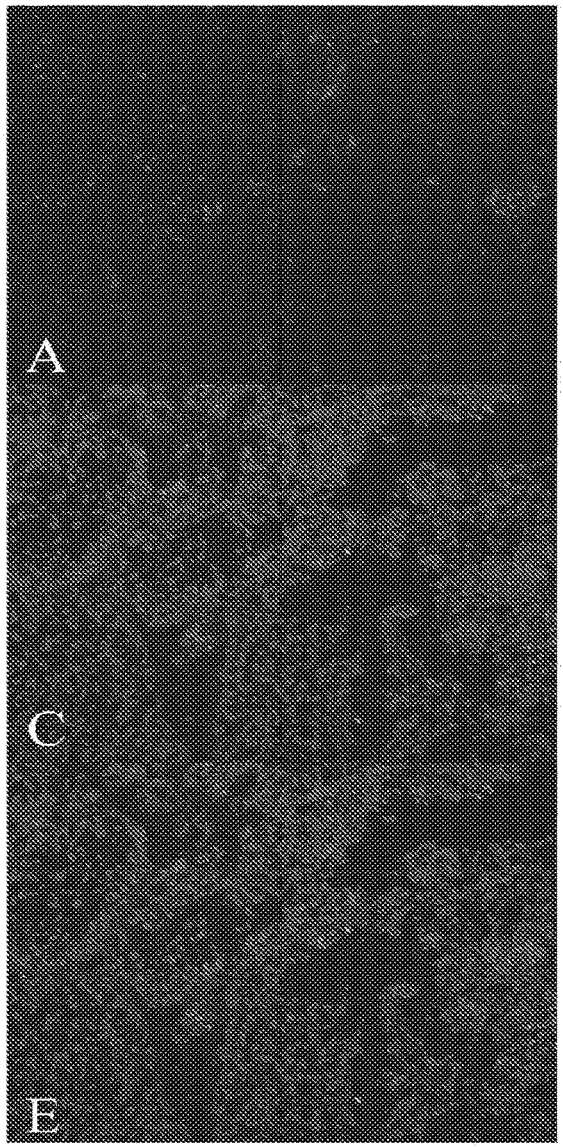
FIG. 3A-F are results of fluorescent in situ hybridization experiments.
Figure 3:
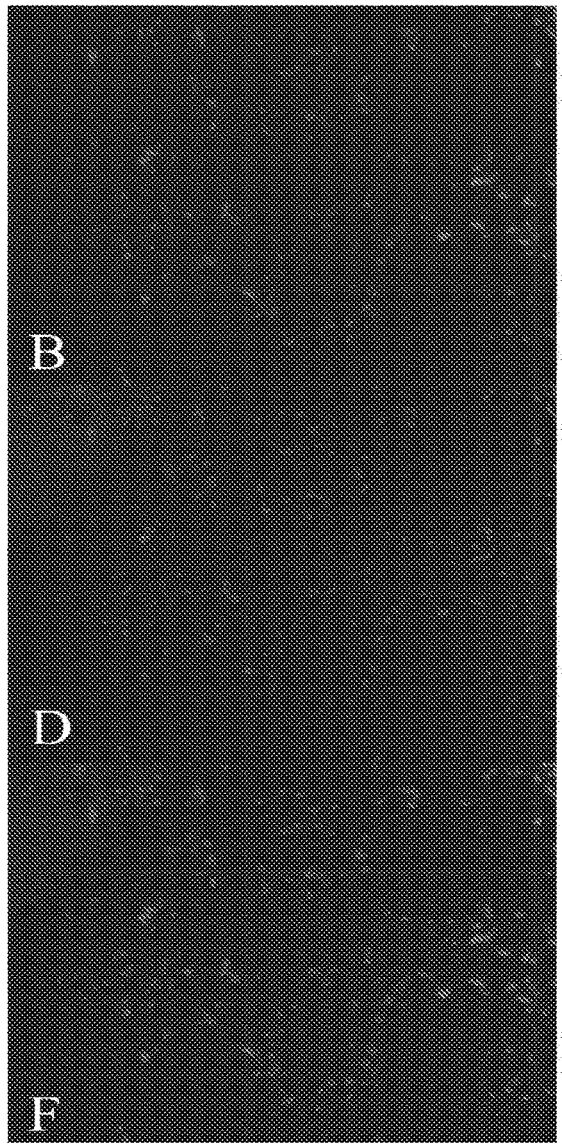

RESULTS: As shown in FIG. 3 the fluorescence in situ hybridization (FISH) results were consistent with the qRT-PCR data. High expression levels of HSFY mRNA were observed in testicular tissue derived from patients with OA. In contrast, expression was markedly decreased in testicular tissue derived from patients with nonobstructive azoospermia who failed microdissection TESE.

Example 4: Statistical Analysis

Statistical analysis was performed with Graphpad Prism Version 5.0c for MAC (Graphpad Software Inc., La Jolla, Calif., USA). Serum FSH, average testicular volume, age, and mean HSFY/PBGD ratio were analyzed with respect to microdissection TESE outcome using the nonparametric Mann-Whitney test. The distribution of testicular histology with respect to microdissection TESE outcome was analyzed with the chi-square test. The performance characteristics of HSFY/PBGD expression ratio measured by qRT-PCR as a diagnostic test to predict the presence of retrievable sperm were determined by receiver-operator characteristic (ROC) curve analysis. We generated ROC curves for the entire cohort and for the Sertoli cell only and maturation arrest subgroups. ROC analysis was not performed for the HS subgroup because sperm were retrieved in all cases. Sensitivities and specificities were calculated using every observed HSFY/PBGD expression ratio as a possible cutoff value to define a positive test. The cutoff values with the best sensitivity and specificity profiles were then selected for the entire cohort and for the Sertoli cell only and maturation arrest subgroups. Likelihood ratios for a positive test result were calculated as sensitivity divided by (1—specificity) and likelihood ratios for a negative result as (1—sensitivity) divided by specificity (Jaeschke et. al. 1994). The probability of sperm retrieval based upon HSFY/PBGD test results was then determined with Fagan's nomogram for Bayes' theorem (Fagan 1975) using the calculated likelihood ratios and the overall and histology-specific sperm retrieval rates at our institution from 1999-2010.

RESULTS: The areas under the ROC curves derived from the qRT-PCR data for the overall study population and for the Sertoli cell only and maturation arrest subgroups were 0.89, 0.98, and 0.90, respectively. Sensitivity and specificity were 67% and 93% for the overall study population, 92% and 100% for the Sertoli cell only subgroup, and 67% and 92% for the maturation arrest subgroup. The estimated probabilities of sperm retrieval for HSFY positive patients were 93% overall, 100% for patients with Sertoli cell only histology, and 91% for patients with maturation arrest. The estimated probabilities of retrieval for HSFY negative patients were 31% overall, 7% for Sertoli cell only patients, and 32% for patients with maturation arrest histology.

Example 5: Semen Analysis

Two semen samples can be collected by masturbation after 2 to 4 days of sexual abstinence. After semen liquefaction at 37 C, standard semen analysis can be performed according to WHO guidelines on one sample to assess sperm concentration, motility, morphology and vitality. The second semen sample can be centrifuged to recover cells within the spun pellet for subsequent RNA extraction. Cells collected can be washed in phosphate buffered saline and immediately frozen in liquid nitrogen until RNA extraction as performed in Example 2.

HSFY RNA expression levels from semen samples can be quantified using quantitative real-time PCR (qRT-PCR) as described in Example 2. Quantified levels of HSFY mRNA expression may predict the presence of retrievable testicular sperm in men with nonobstructive azoospermia (NOA) in the same manner as seen in Example 2 for testicular tissue.

Example 6: Successful Sperm Retrieval from Patients with High HSFY Expression Levels Fifty-four men with nonobstructive azoospermia (NOA) and nine men with obstructive azoospermia (OA) underwent microdissection TESE, diagnostic testis biopsy, and simultaneous extraction of seminiferous tubular tissue for research. Clinical data was prospectively collected, including testicular histopathology and results of microdissection TESE. The level of HSFY expression in each patient was measured by multiplex quantitative real-time PCR (qRT-PCR), using PBGD as the reference housekeeping gene. The performance characteristics of HSFY mRNA detection by qRT-PCR were evaluated with receiver-operator characteristic (ROC) curves. The probabilities of sperm retrieval were calculated based upon HSFY testing from the sensitivity and specificity of HSFY testing and the sperm retrieval rates at the inventors' institution from 1999-2010. The quantitative RT-PCR data was corroborated by analysis of HSFY mRNA expression in testicular tissue with fluorescent in situ hybridization (FISH).

Clinical features of the study population are presented in Table 1. Sperm were retrieved in 27/54 (50%) cases. Study patients in whom sperm were retrieved had higher serum FSH values (p=0.016), lower average testicular volumes (p=0.037), a different distribution of testicular histology, and similar ages (p=0.910) when compared to patients who failed microdissection TESE.

TABLE 1

Clinical parameters of the study patients

|  | NOA, sperm retrieved (n = 27) | NOA, sperm not retrieved (n = 27) | P-Value |
|---|---|---|---|
| Age (years)* | 34.6 (31.4-37.8) | 33.4 (31.6-35.2) | .910 |
| Serum FSH (IU/L)* | 23.9 (18.9-28.8) | 16.7 (11.9-21.5) | .016 |
| Average Testicular *Volume (mL) | 9.0 (7.0-11.0) | 11.8 (10.1-13.5) | .037 |
| Histology (# patients) | SCO 12<br>MA 6<br>HS 9 | SCO 15<br>MA 12<br>HS 0 | .0035 |

*Values are given as means (95% confidence intervals)

Figure 1D:
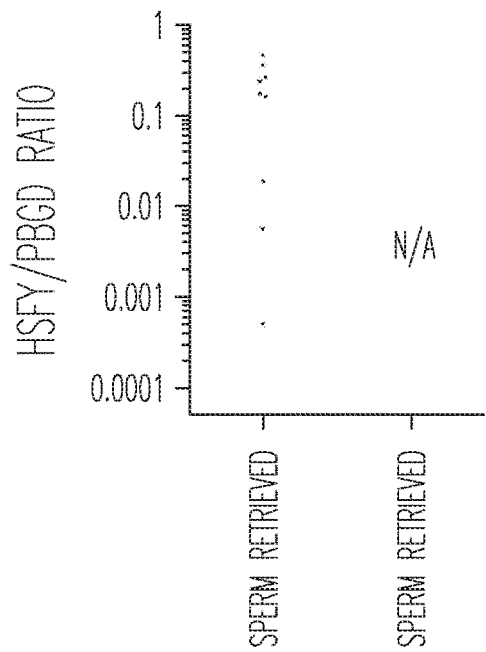

The mean weight of testis tissue used for quantitative expression analysis of HSFY transcript variant 1 mRNA was 78.1 (range 10-240) mg. Sufficient RNA for purification and qRT-PCR was extracted in all cases. The mean HSFY/PBGD expression ratio in the control patients with azoospermia was 0.673 (standard error $2.56 \times 10^{-2}$, range 0.145-0.946). The HSFY/PBGD expression ratios in nonobstructive azoospermia patients with respect to microdissection TESE outcome are presented in FIG. 1 and Table 2.

TABLE 2

HSFY/PBGD expression ratios in NOA patients with respect to TESE outcome.

|  | NOA, sperm retrieved (n = 27) | NOA, sperm not retrieved (n = 27) | P-Value |
|---|---|---|---|
| All patients | $7.76 \times 10^{-2} \pm 2.47 \times 10^{-2}$ | $1.90 \times 10^{-3} \pm 8.00 \times 10^{-4}$ | <.0001 |
| SCO | $5.70 \times 10^{-2} \pm 1.5 \times 10^{-3}$ | $6.00 \times 10^{-4} \pm 1.00 \times 10^{-4}$ | <.0001 |
| MA | $6.52 \times 10^{-2} \pm 4.76 \times 10^{-2}$ | $3.60 \times 10^{-3} \pm 1.60 \times 10^{-3}$ | .0076 |
| HS | $1.82 \times 10^{-2} \pm 5.26 \times 10^{-2}$ | n/a | n/a |

Values are given as means ± standard errors.

Significantly higher HSFY/PBGD expression ratios were observed in patients with successful microdissection TESE when compared to those with failed microdissection TESE within the overall study population, and within the Sertoli cell only (SCO) and maturation arrest subgroups. Comparison was not possible for the HS subgroup because sperm were retrieved in all cases. However, HSFY/PBGD expression ratios were high or very high in 8/9 patients with HS histology. The one patient with HS who had a low expression ratio was a patient with an AZFc deletion in whom diagnostic biopsy revealed that 98% of tubules were Sertoli cell only (SCO) pattern, and only 2% of tubules contained very rare mature sperm.

Figure 2A:
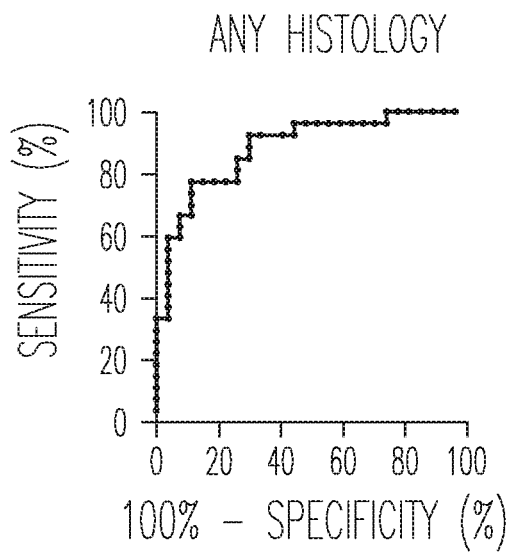
FIG. 2A-C show receiver operator characteristic curves for HSFY mRNA detection by quantitative RT PCR to predict the presence of retrievable testicular sperm amongst various patient groups, including the all nonobstructive azoospermia (NOA) patients in the study (FIG. 2A), the Sertoli cell only patients (FIG. 2B) and the maturation arrest patients (FIG. 2C).
Figure 2B:
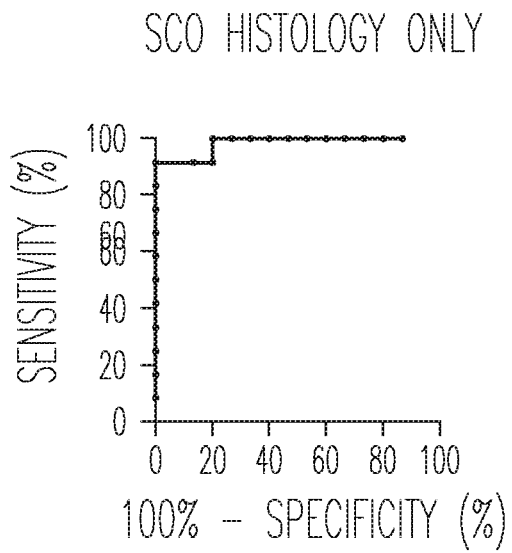
Figure 2C:
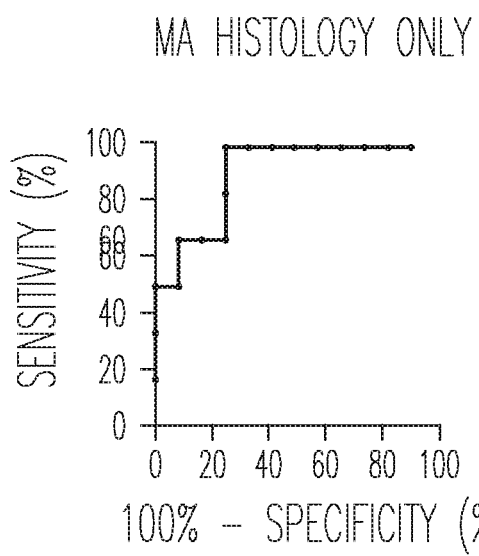

ROC curves are presented in FIG. 2. The areas under the curves (AUC) for the entire cohort, the Sertoli cell only (SCO) subgroup, and the maturation arrest subgroup were 0.89, 0.98, and 0.90, respectively. The optimal cut off values for a positive HSFY/PBGD expression ratio were HSFY/PBGD expression ratio >4.48×10$^{-3}$ for the entire cohort, HSFY/PBGD expression ratio >1.20×10$^{-3}$ for the Sertoli cell only (SCO) subgroup, and HSFY/PBGD expression ratio >7.40×10$^{-3}$ for the maturation arrest subgroup.

The performance characteristics of HSFY/PBGD expression ratio detected by RT-PCR as a diagnostic test to predict the presence of retrievable sperm during microdissection TESE using the selected cutoff values for the overall study population, and the Sertoli cell only (SCO) and maturation arrest subgroups are presented in Table 3. The post-test probabilities of sperm retrieval were derived from the calculated likelihood ratios and the overall sperm retrieval rates (SRRs) observed at Weill Cornell Medical College using Fagan's nomogram for Bayes' theorem (Fayes 1975). Sensitivity and specificity were 67% and 93% for the overall study population, 92% and 100% for the Sertoli cell only (SCO) subgroup, and 67% and 92% for the maturation arrest subgroup. The estimated probabilities of sperm retrieval for HSFY positive patients were 93% overall, 100% for patients with Sertoli cell only (SCO) histology, and 91% for patients with maturation arrest. The estimated probabilities of retrieval for HSFY negative patients were 31% overall, 7% for Sertoli cell only patients, and 32% for patients with maturation arrest histology.

Table 3 shows the test characteristics of the HSFY/PBGD ratio to predict sperm retrieval based upon the optimal cutoff values selected for the overall study population, and the Sertoli cell only and maturation arrest subgroups.

clinically useful in the management of patients with nonobstructive azoospermia. The Examples described herein demonstrate that the level of HSFY transcript variant 1 mRNA detected by qRT-PCR in testicular tissue is highly predictive of microdissection TESE outcome in men with nonobstructive azoospermia, wherein men with higher levels of HSFY are more likely to experience successful sperm retrieval. Similarly, observation by fluorescence in situ hybridization assay, also showed this relationship.

The HSFY/PBGD ratio has potential to be used in combination with testicular histopathology and institutional SRRs to accurately counsel individual patients about their chances of sperm retrieval. The benefit of HSFY testing is illustrated by considering the case of a genetically normal patient with idiopathic nonobstructive azoospermia whose diagnostic biopsy shows Sertoli cell only pattern. In the absence of HSFY testing, this patient would be counseled that his chance of successful sperm retrieval is 40-50%. Nearly all men in this scenario elect to proceed with microdissection TESE given the reasonably high chance of success.

However, if such a patient tested positive for HSFY expression, he could be counseled that the chance of sperm retrieval is close to 100%. Conversely, if he were to test negative the estimated chance of sperm retrieval would be 7%. Considering the 29-40% ongoing pregnancy rates reported in IVF-ICSI cycles using testicular sperm from men with nonobstructive azoospermia (Nicopoullos et. al. 2004), the chance of achieving an ongoing pregnancy in such a

TABLE 3

Test characteristics of HSFY/PBGD ratio to predict sperm retrieval

| | Sensitivity | Specificity | Positive Likelihood Ratio | Negative Likelihood Ratio | Institutional SRR (1999-2010) | Estimated probability of sperm retrieval for an individual patient[a] |
|---|---|---|---|---|---|---|
| All patients | 66.7% | 92.6% | 9.0 | 0.36 | 56.6% (606/1070) | HSFY+: 93% HSFY−: 31% |
| SCO | 91.7% | 100% | infinity | 0.08 | 48.3% (253/524) | HSFY+: 100% HSFY−: 7% |
| MA | 66.7% | 91.7% | 3.3 | 0.36 | 56.1% (92/164) | HSFY+: 91% HSFY−: 32% |
| HS | n/a | n/a | n/a | n/a | 94.3% (149/158) | n/a |

[a]The Estimated probability of sperm retrieval for an individual patient was derived using Fagan's nomogram for Bayes' theorem (Jaeschke et al. JAMA 271: 703-707 (1994)).

Fluorescence in situ hybridization (FISH) studies corroborated the qRT-PCR results. A high expression of HSFY mRNA was observed in seminiferous tubular tissue from both patients with azoospermia (FIG. 3A). Expression was localized to the nuclei of germ cells and Sertoli cells. In contrast, we observed low HSFY mRNA expression in testicular tissue from nonobstructive azoospermia patients who failed microdissection TESE. Faint expression was seen in Sertoli cell nuclei in one of these patients (FIG. 3B), and expression was not detected in the other patient.

Two copies of the HSFY gene are present within palindrome P4 of the AZFb region of the Y chromosome (Repping et. al. 2002). These genes encode three different mRNA transcripts that are expressed in human testis. Only the protein translated from transcript variant 1 contains a heat shock factor-like DNA binding domain (Tessari et. al. 2004), which suggests that this mRNA is the critical HSFY transcript. The function of HSFY has not yet been elucidated.

Regardless of how the HSFY gene functions, this disclosure shows that the detection of HSFY mRNA can be patient would be 2-3%. While some men might still elect to proceed with microdissection TESE in this scenario, the medical risks and financial expenses may not be justified.

While the testicular tissue for RNA extraction used in this study was obtained by microsurgical open testicular biopsy under general anesthesia, other less invasively obtained samples and obtainable by less specialized physicians can be used. For example, office-based testicular sampling for histological assessment and sperm retrieval is already well established. Large-needle percutaneous aspiration biopsy is simple, safe and on average yields 385 mg of testicular tissue (Carpi et. al. 2006). Given the 10-240 mg range of biopsy weights used in this analysis, application of HSFY testing to percutaneously obtained testicular tissue is reasonable. Patients could undergo one simple, office-based procedure during which tissue could be procured for simultaneous histological assessment and HSFY testing, and during which a limited attempt could be made at therapeutic sperm retrieval. Similarly, semen samples can also be used, which are even less invasively obtained, and their use could greatly enhance the clinical utility of this test.

Thus, quantification of HSFY mRNA in testicular tissue or semen may significantly improve a fertility physician's ability to counsel patients with nonobstructive azoospermia and to select patients for microdissection TESE. Such methods may help to minimize the number of futile attempts at testicular sperm retrieval, and to increase the likelihood that sperm retrieval will be successful in nonobstructive azoospermia cases when HSFY mRNA expression is successfully detected.

Example 7: HSFY RNA Detection in Semen

Figure 4:
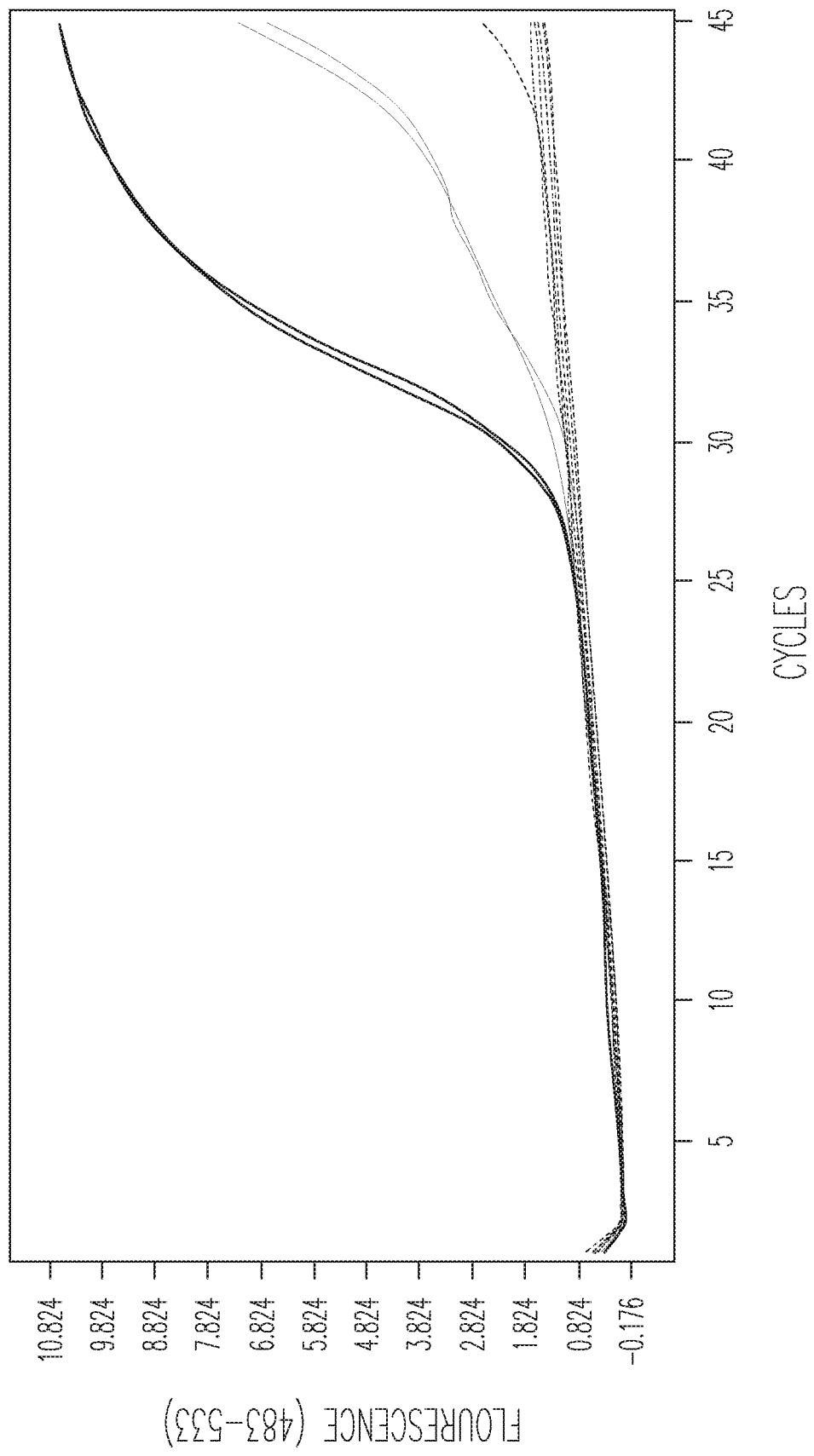
FIG. 4 is a graph of the amount of amplified qRT-PCR product as measured by as a function of amplification cycle, where the top two heavy solid lines show the fluorescence detected from amplification of mRNA from a normal semen sample, the middle two light solid lines show the fluorescence detected from amplification of mRNA from a semen sample of a male with a vasectomy, and the bottom dashed lines are a control. As illustrated, HSFY amplification was much earlier and more robust in the normal semen sample.

This Example describes experiments for evaluating the technical feasibility of HSFY RNA detection in semen.
Methods:
RNA was extracted (using a Roche High Pure RNA Isolation Kit) from 200 uL of whole semen from one patient with 220 million sperm/mL, and from another patient with rare motile sperm after vasectomy (67 sperm per 100 uL, occasional motile sperm). RNA was reverse transcribed to cDNA (Transcriptor First Strand DNA Synthesis Kit, Roche). The cDNA synthesis reaction was also carried out in the absence of reverse transcriptase to generate negative control cDNA. qRT-PCR was performed for HSFY and the housekeeping gene PBGD (which served as a positive control) using the Universal Probe Library detection platform on the LightCycler 480 instrument.
Results:
FIG. 4 shows the amplification of HSFY in the normal semen versus the semen from the male with a vasectomy. As illustrated, HSFY amplification was much earlier and more robust in the normal sample.

HSFY detection in semen is therefore technically feasible. These preliminary results indicate that semen samples may be used for analysis of HSFY expression levels to distinguish between men with normal sperm concentrations and men with azoospermia.

REFERENCES

1. Hodgson N C, Button J, Solorzano C C. Thyroid cancer: is the incidence still increasing? Ann Surg Oncol 2004; 11:1093-7.
2. Cooper D S, Doherty G M, Haugen B R, Kloos R T, Lee S L, Mandel S J, et al. Management guidelines for patients with thyroid nodules and differentiated thyroid cancer. Thyroid 2006; 16:109-42.
3. Wang C, Crapo L M. The epidemiology of thyroid disease and implications for screening. Endocrinol Metab Clin North Am 1997; 26:189-218.
4. Faggiano A, Caillou B, Lacroix L, Talbot M, Filetti S, Bidart J M, et al. Functional characterization of human thyroid tissue with immunohistochemistry. Thyroid 2007; 17:203-11.
5. Mazzaferri E L. Thyroid cancer in thyroid nodules: finding a needle in the haystack. Am J Med 1992; 93:359-62.
6. Robertson M L, Steward D L, Gluckman J L, Welge J. Continuous laryngeal nerve integrity monitoring during thyroidectomy: does it reduce risk of injury? Otolaryngol Head Neck Surg 2004; 131:596-600.
7. Bartel D P. MicroRNAs: target recognition and regulatory functions. Cell 2009; 136:215-33.
8. Wiemer E A. The role of microRNAs in cancer: no small matter. Eur J Cancer 2007; 43:1529-44.
9. Gao Y, Wang C, Shan Z, Guan H, Mao J, Fan C, et al. miRNA expression in a human papillary thyroid carcinoma cell line varies with invasiveness. Endocr J 2010; 57:81-6.
10. Menon M P, Khan A. Micro-RNAs in thyroid neoplasms: molecular, diagnostic and therapeutic implications. J Clin Pathol 2009; 62:978-85.
11. Nikiforova M N, Chiosea S I, Nikiforov Y E. MicroRNA expression profiles in thyroid tumors. Endocr Pathol 2009; 20:85-91.
12. He H, Jazdzewski K, Li W, Liyanarachchi S, Nagy R, Volinia S, et al. The role of microRNA genes in papillary thyroid carcinoma. Proc Natl Acad Sci USA 2005; 102: 19075-80.
13. Pallante P, Visone R, Croce C M, Fusco A. Deregulation of microRNA expression in follicular-cell-derived human thyroid carcinomas. Endocr Relat Cancer 2010; 17:F91-104.
14. Sheu S Y, Grabellus F, Schwertheim S, Worm K, Broecker-Preuss M, Schmid K W. Differential miRNA expression profiles in variants of papillary thyroid carcinoma and encapsulated follicular thyroid tumours. Br J Cancer 2010; 102:376-82.
15. Chen Y T, Kitabayashi N, Zhou X K, Fahey T J, 3rd, Scognamiglio T. MicroRNA analysis as a potential diagnostic tool for papillary thyroid carcinoma. Mod Pathol 2008; 21:1139-46.
16. Nikiforova M N, Tseng G C, Steward D, Diorio D, Nikiforov Y E. MicroRNA expression profiling of thyroid tumors: biological significance and diagnostic utility. J Clin Endocrinol Metab 2008; 93:1600-8.
17. Pallante P, Visone R, Ferracin M, Ferraro A, Berlingieri M T, Troncone G, et al. MicroRNA deregulation in human thyroid papillary carcinomas. Endocr Relat Cancer 2006; 13:497-508.
18. Visone R, Russo L, Pallante P, De Martino I, Ferraro A, Leone V, et al. MicroRNAs (miR)-221 and miR-222, both overexpressed in human thyroid papillary carcinomas, regulate p27Kip1 protein levels and cell cycle. Endocr Relat Cancer 2007; 14:791-8.
19. Weber F, Teresi R E, Broelsch C E, Frilling A, Eng C. A limited set of human MicroRNA is deregulated in follicular thyroid carcinoma. J Clin Endocrinol Metab 2006; 91:3584-91.
20. Duda R. Pattern Classification. 2nd Edition ed: Willey-Interscience; 2000.
21. Venables W. Modern Applied Statistics with S (Statistics and Computing): Springer; 2010.
22. Gharib H. Changing trends in thyroid practice: understanding nodular thyroid disease. Endocr Pract 2004; 10:31-9.
23. Hegedus L. Clinical practice. The thyroid nodule. N Engl J Med 2004; 351:1764-71.
24. Layfield L J, Cibas E S, Baloch Z. Thyroid fine needle aspiration cytology: a review of the National Cancer Institute state of the science symposium. Cytopathology 2010; 21:75-85.
25. Nikiforov Y E, Steward D L, Robinson-Smith T M, Haugen B R, Klopper J P, Zhu Z, et al. Molecular testing for mutations in improving the fine-needle aspiration diagnosis of thyroid nodules. J Clin Endocrinol Metab 2009; 94:2092-8.
26. Xing M, Clark D, Guan H, Ji M, Dackiw A, Carson K A, et al. BRAF mutation testing of thyroid fine-needle aspiration biopsy specimens for preoperative risk stratification in papillary thyroid cancer. J Clin Oncol 2009; 27:2977-82.

27. Nikiforova M N, Nikiforov Y E. Molecular diagnostics and predictors in thyroid cancer. Thyroid 2009; 19:1351-61.
28. Eszlinger M, Paschke R. Molecular fine-needle aspiration biopsy diagnosis of thyroid nodules by tumor specific mutations and gene expression patterns. Mol Cell Endocrinol 2010; 322:29-37.
29. Sapio M R, Posca D, Raggioli A, Guerra A, Marotta V, Deandrea M, et al. Detection of RET/PTC, TRK and BRAF mutations in preoperative diagnosis of thyroid nodules with indeterminate cytological findings. Clin Endocrinol (Oxf) 2007; 66:678-83.
30. Zatelli M C, Trasforini G, Leoni S, Frigato G, Buratto M, Tagliati F, et al. BRAF V600E mutation analysis increases diagnostic accuracy for papillary thyroid carcinoma in fine-needle aspiration biopsies. Eur J Endocrinol 2009; 161:467-73.
31. Kebebew E, Peng M, Reiff E, Duh Q Y, Clark O H, McMillan A. ECM1 and TMPRSS4 are diagnostic markers of malignant thyroid neoplasms and improve the accuracy of fine needle aspiration biopsy. Ann Surg 2005; 242:353-61; discussion 61-3.
32. Kebebew E, Peng M, Reiff E, McMillan A. Diagnostic and extent of disease multigene assay for malignant thyroid neoplasms. Cancer 2006; 106:2592-7.
33. Barden C B, Shister K W, Zhu B, Guiter G, Greenblatt D Y, Zeiger M A, et al. Classification of follicular thyroid tumors by molecular signature: results of gene profiling. Clin Cancer Res 2003; 9:1792-800.
34. Prasad N B, Somervell H, Tufano R P, Dackiw A P, Marohn M R, Califano J A, et al. Identification of genes differentially expressed in benign versus malignant thyroid tumors. Clin Cancer Res 2008; 14:3327-37.
35. Finley D J, Lubitz C C, Wei C, Zhu B, Fahey T J, 3rd. Advancing the molecular diagnosis of thyroid nodules: defining benign lesions by molecular profiling. Thyroid 2005; 15:562-8.
36. Mazzanti C, Zeiger M A, Costouros N G, Umbricht C, Westra W H, Smith D, et al. Using gene expression profiling to differentiate benign versus malignant thyroid tumors. Cancer Res 2004; 64:2898-903.
37. Mazeh H, Mizrahi I, Halle D, Ilyayev N, Stojadinovic A, Trink B, et al. Development of a microRNA-based molecular assay for the detection of papillary thyroid carcinoma in aspiration biopsy samples. Thyroid 2011; 21:111-8.
38. Kitano M, Rahbari R, Patterson E E, Xiong Y, Prasad N B, Wang Y, et al. Expression profiling of difficult-to-diagnose thyroid histologic subtypes shows distinct expression profiles and identify candidate diagnostic microRNAs. Ann Surg Oncol 2011; 18:3443-52.
39. Frezzetti D, Menna M D, Zoppoli P, Guerra C, Ferraro A, Bello A M, et al. Upregulation of miR-21 by Ras in vivo and its role in tumor growth. Oncogene 2010.
40. Jazdzewski K, Boguslawska J, Jendrzejewski J, Liyanarachchi S, Pachucki J, Wardyn K A, et al. Thyroid Hormone Receptor {beta} (THRB) Is a Major Target Gene for MicroRNAs Deregulated in Papillary Thyroid Carcinoma (PTC). J Clin Endocrinol Metab 2010.
Carpi A, Fabris F G, Todeschini G, et al. Large needle percutaneous aspiration biopsy of the testicle in men with nonobstructive azoospermia: technical performance. Biomed Pharmacother. 2006; 60(9):557-560.
Carpi A, Sabanegh E, Mechanick J. Controversies in the management of nonobstructive azoospermia. Fertil Steril. 2009; 91(4):963-970.
Donoso P, Tournaye H, Devroey P. Which is the best sperm retrieval technique for non-obstructive azoospermia? A systematic review. Hum Reprod Update. 2007; 13(6):539-549.
Ferlin A, Speltra E, Patassini C, Pati M A, Garolla A, Caretta N, Foresta C. Heat shock protein and heat shock factor expression in sperm: relation to oligozoospermia and varicocele. J. Urol. 2010; 183(3):1248-52. Epub 2010 Jan. 22.
Fagan T J. Letter: Nomogram for Bayes theorem. N Engl J Med. 1975; 293(5):257.
Jaeschke R, Guyatt G H, Sackett D L. Users' guides to the medical literature. III. How to use an article about a diagnostic test. B. What are the results and will they help me in caring for my patients? The Evidence-Based Medicine Working Group. JAMA. 1994; 271 (9):703-707.
Kleiman S E, Lagziel A, Yogev L, Botchan A, Paz G, Yavetz H. Expression of CDY1 may identify complete spermatogenesis. Fertil Steril. 2001; 75(1):166-173.
Meng M V, Cha I, Ljung B M, Turek P J. Relationship between classic histological pattern and sperm findings on fine needle aspiration map in infertile men. Hum Reprod. 2000; 15(9):1973-1977.
Nicopoullos J D, Gilling-Smith C, Almeida P A, Norman-Taylor J, Grace I, Ramsay J W. Use of surgical sperm retrieval in azoospermic men: a meta-analysis. Fertil Steril. 2004; 82(3):691-701.
Nicopoullos J D, Gilling-Smith C, Almeida P A, Norman-Taylor J, Grace I, Ramsay J W. Use of surgical sperm retrieval in azoospermic men: a meta-analysis. Fertil Steril. 2004; 82(3):691-701.
Ramasamy R. Yagan N, Schlegel P N. Structural and functional changes to the testis after conventional versus microdissection testicular sperm extraction. Urology. 2005; 65(6):1190-1194.
Repping S, Skaletsky H, Lange J, et al. Recombination between palindromes P5 and P1 on the human Y chromosome causes massive deletions and spermatogenic failure. Am J Hum Genet. 2002; 71(4):906-922.
Schlegel P N. Testicular sperm extraction: microdissection improves sperm yield with minimal tissue excision. Hum Reprod. 1999; 14(1): 131-135.
Schlegel P N. Testicular sperm extraction: microdissection improves sperm yield with minimal tissue excision. Hum Reprod. 1999; 14(1):131-135.
Shinka T, Sato Y, Chen G. et al. Molecular characterization of heat shock-like factor encoded on the human Y chromosome, and implications for male infertility. Biol Reprod. 2004; 71(1):297-306.
Song G J, Lee H, Park Y, et al. Expression pattern of germ cell-specific genes in the testis of patients with nonobstructive azoospermia: usefulness as a molecular marker to predict the presence of testicular sperm. Fertil Steril. 2000; 73(6):1104-1108.
Stahl P J, Mielnik A, Schlegel P N, Paduch D A. Testicular expression analysis of the AZF genes in azoospermic men suggests essentiality and specific function for DDX3Y, RPS4Y2, CDY2, and HSFY Fertility and Sterility. 2010; 94(4):S232.
Stahl P J, Masson P, Mielnik A, Marean M B, Schlegel P N, Paduch D A. A decade of experience emphasizes that testing for Y microdeletions is essential in American men with azoospermia and severe oligozoospermia. Fertil Steril. 2010; 94(5):1753-1756.
Su L M, Palermo G D, Goldstein M, Veeck L L, Rosenwaks Z, Schlegel P N. Testicular sperm extraction with intracytoplasmic sperm injection for nonobstructive azoospermia: testicular histology can predict success of sperm retrieval. *J. Urol.* 1999; 161(1):112-116.

Tessari A, Salata E, Ferlin A, Bartoloni L, Slongo M L, Foresta C. Characterization of HSFY, a novel AZFb gene on the Y chromosome with a possible role in human spermatogenesis. *Mol Hum Reprod.* 2004; 10(4):253-258.

Tsujimura A, Matsumiya K, Miyagawa Y, et al. Prediction of successful outcome of microdissection testicular sperm extraction in men with idiopathic nonobstructive azoospermia. *J. Urol.* 2004; 172(5 Pt 1):1944-1947.

Tsujimura A, Matsumiya K, Miyagawa Y, et al. Conventional multiple or microdissection testicular sperm extraction: a comparative study. *Hum Reprod.* 2002; 17(11): 2924-2929.

Vogt P H, Falcao C L, Hanstein R, Zimmer J. The AZF proteins. *Int J. Androl.* 2008; 31(4):383-394.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The specific methods, devices and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention.

The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "an antibody" or "a nucleic acid" or "a polypeptide" includes a plurality of such antibodies, nucleic acids or polypeptides (for example, a solution of antibodies, nucleic acids or polypeptides or a series of antibody, nucleic acid or polypeptide preparations), and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

The following statements are intended to describe some aspects of the invention.

STATEMENTS OF THE INVENTION

1. A method for assessing whether sperm can be retrieved from a male comprising:
   obtaining a quantified expression level of HSFY in the test sample to generate a HSFY quantified test result;
   wherein sperm can be retrieved from the male when the HSFY quantified test result is detectably higher than the quantified baseline HFSY expression level.

2. A method for assessing whether sperm can be retrieved from a male comprising:
   a) obtaining a test sample;
   b) obtaining a quantified expression level of HSFY in the test sample to generate a HSFY quantified test result;
   wherein sperm can be retrieved from the male when the HSFY quantified test result is detectably higher than the quantified baseline HFSY expression level.

3. The method of statement 1 or 2, comprising comparing the HSFY quantified test result with a quantified baseline HFSY expression level;

4. The method of any of statements 1-3, wherein the test sample is blood, urine, semen, testicular tissue or a combination thereof.

5. The method of any of statements 1-4, wherein the test sample is semen or testicular tissue.

6. The method of any of statements 1-5, wherein the test sample is testicular tissue.

7. The method of any of statements 1-6, wherein obtaining a quantified expression level of HSFY comprises polymerase chain reaction (PCR), reverse transcription, quantitative reverse-transcriptase-polymerase-chain-reaction (RT-PCR), serial analysis of gene expression (SAGE), northern blot analysis, in situ hybridization, or combinations thereof.

8. The method of any of statements 1-7, wherein obtaining a quantified expression level of HSFY comprises contacting the test sample with an anti-HSFY antibody, and observing a signal if an HSFY-antibody complex forms.

9. The method of statement 8, wherein the method comprises Western blotting, enzyme-linked immunosorbent assays (ELISAs), radioimmunoassay, immunocytochemistry, immunohistochemistry, flow cytometry, immunoprecipitation, one-dimensional electrophoresis, two-dimensional electrophoresis, mass spectroscopy, detection of enzymatic activity and combinations thereof.

10. The method of any of statements 1-9, wherein obtaining a quantified expression level of HSFY in the test sample further comprises obtaining a quantified expression level of a control.

11. The method of statement 10, wherein the control facilitates normalization of inter-sample isolation and handling variations.

12. The method of statement 10 or 11, wherein the control is a housekeeping gene.

13. The method of statement 12, wherein the housekeeping gene is ubiquitin C, beta-actin, GAPDH, 18S ribosomal RNA (18S rRNA), porphobilinogen-deaminase (PBGD) or a combination thereof.

14. The method of statement 12 or 13, wherein the housekeeping gene porphobilinogen-deaminase (PBGD).

15. The method of any of statements 1-14, wherein the HSFY quantified test result is a ratio of IISFY to PBGD expression levels.

16. The method of any of statements 1-15, wherein the baseline is a quantified expression level of HSFY in a male, or a collection of males, where sperm retrieval was unsuccessful.

17. The method of any of statements 1-16, wherein the baseline is a range of quantified expression levels of HSFY in a collection of males, where sperm retrieval was unsuccessful.

18. The method of any of statements 1-17, wherein the baseline is a quantified expression level of HSFY in a male, or a collection of males, with nonobstructive azoospermia and/or AZFb microdeletions.

19. The method of any of statements 1-18, wherein the baseline is a mean±95% confidence interval of a group of quantified HSFY expression values observed in males where sperm retrieval was not successful.

20. The method of any of statements 1-19, wherein the baseline a mean±95% confidence interval of a group of quantified HSFY expression values observed in males with nonobstructive azoospermia and with AZFb microdeletions.

21. The method of any of statements 1-20, wherein the HSFY quantified test result is detectably higher than the quantified baseline HFSY expression level, when the HSFY quantified test result is 10%, 15%, 20%, 25%, 30%, 35%, 40%, 45%, 50%, 55%, 60%, 65%, 70%, 75%, 80%, 85%, 90%, 95%, 100%, or 150% higher than the quantified baseline HFSY expression level.

22. The method of any of statements 1-21, wherein the HSFY quantified test result is detectably higher than the quantified baseline HFSY expression level, when the HSFY quantified test result is two-fold, three-fold, four-fold, five-fold, six-fold, seven-fold, eight-fold, nine-fold, or ten-fold higher than the quantified baseline IIFSY expression level.

23. The method of any of statements 1-22, wherein comparing the HSFY quantified test result with a quantified baseline HFSY expression level comprises processor evaluation, display and/or output.

24. The method of any of statements 1-23, wherein comparing the HSFY quantified test result with a quantified baseline HFSY expression level comprises computer evaluation, display and/or output.

25. The method of any of statements 1-24, further comprising retrieving sperm from the male.

26. A method for determining the likelihood of sperm retrieval from a male with nonobstructive azoospermia consisting of the steps:
a) obtaining a sample of testicular tissue or semen from the male
b) determining the level of expression of IISFY in the sample
c) comparing the level of HSFY expression in the sample with that obtained from men with nonobstructive azoospermia and failed sperm retrieval
wherein a higher level of expression of HSFY in the sample predicts the likelihood of sperm retrieval from the male.

27. A kit for assessing whether sperm can be retrieved from a male comprising:
a) one or more reagents for quantifying HSFY expression levels in a test sample from the male to obtain a HSFY quantified test result; and
b) instructions for evaluating the HSFY quantified test result to determine whether sperm can be retrieved from the male.

28. The kit of statement 27, comprising reagents for stabilizing and/or isolating RNA.

29. The kit of statement 28, wherein the RNA is in a test sample selected from the group consisting of blood, urine, semen, testicular tissue and a combination thereof.

30. The kit of any of statements 27-29, comprising reagents for microarray analysis, Northern blotting, nuclease protection assays, RNA fingerprinting, polymerase chain reaction, ligase chain reaction, Qbeta replicase, isothermal amplification method, strand displacement amplification, transcription based amplification systems, quantitative nucleic acid amplification assays (e.g., polymerase chain reaction assays), combined reverse transcription/nucleic acid amplification, nuclease protection (SI nuclease or RNAse protection assays), Serial Analysis Gene Expression (SAGE).

31. The kit of any of statements 27-30, comprising at least one primer or probe that can selectively hybridize to HSFY mRNA.

32. The kit of statement 31, wherein the at least one primer or probe selectively hybridizes to HSFY mRNA under stringent hybridization conditions.

33. The kit of statement 32, wherein the stringent hybridization conditions comprise hybridization in 6× sodium chloride/sodium citrate (SSC) at about 45° C., followed by one or more washes in 0.2×SSC, 0.1% SDS.

34. The kit of statement 32 or 33, wherein the stringent hybridization conditions comprise hybridization followed by at least one wash at 50° C., 55° C., 60° C., 65° C., 65° C. or a combination thereof.

35. The kit of any of statements 27-34, wherein the HSFY is an mRNA encoding an amino acid sequence selected from the group consisting of SEQ ID NO: 2 and 4.

36. The kit of any of statements 31-35, wherein the at least one primer or probe comprises any of

```
                                    (SEQ ID NO: 5)
          GTCAATGAGGCTCCATATCGT-3', (SEQ ID NO: 6)
          GATCGTAGGCATTTGCAACC-3', (SEQ ID NO: 7)
          5'-TCAGAAGCCTCCACTAGGTCTCCA-3',

SEQ ID NO: 8)
          TGACAGAAAGGTGGCTAGAAAGGCA-3',
``` or a combination thereof.

37. The kit of any of statements 27-36, comprising an enzyme useful for quantifying HSFY expression levels.

38. The kit of statement 37, wherein the enzyme is a reverse transcriptase, a DNA polymerase, a heat-tolerant DNA polymerase, a ligase, a restriction enzyme or a combination thereof.

39. The kit of statement 37 or 38, wherein each enzyme is packaged separately.

40. The kit of statement 27, comprising reagents for stabilizing and/or isolating HSFY protein.

41. The kit of statement 27 or 40, comprising an anti-IISFY antibody.

42. The kit of any of statements 27, 40 or 41, comprising reagents for Western blotting, enzyme-linked immunosorbent assays (ELISAs), radioimmunoassay, immunocytochemistry, immunohistochemistry, flow cytometry, immunoprecipitation, one- and two-dimensional electrophoresis, mass spectroscopy, detection of enzymatic activity.

43. The kit of any of statements 27, 40-42, comprising a solid support with an anti-HSFY antibody covalently or non-covalently bound thereto.

44. The kit of statement 43, comprising an antibody for a control protein covalently or non-covalently bound to a location distinct from a location for the anti-HSFY antibody.

45. The kit of any of statements 27-42, further comprising tissue collection means selected from the group consisting of tissue stabilizing reagents, needles, scalpels, gloves, test tubes, buffers, semen collection vessels, and combinations thereof.

46. The of any of statements 27-45, further comprising slides, cover slips, stains and/or reagents for cytology.

Other embodiments are within the following claims.

The invention claimed is:

1. A method comprising retrieving sperm from a male with a HSFY quantified test result that is at least five-fold higher than a baseline HFSY expression level, where the HSFY quantified test result is determined by a method comprising:

quantifying an expression level of HSFY by measuring the amount of HSFY RNA in a test sample from the male using at least one primer with a sequence selected from SEQ ID NO:5, 6, 7, or 8, and normalizing the measured HSFY RNA amount to a measured amount of RNA from a housekeeping gene to generate a HSFY quantified test result; and comparing the HSFY quantified test result to a baseline HFSY expression level to identify test samples with HSFY quantified test results that are at least five-fold higher than a quantified baseline HFSY expression level.

2. The method of claim 1, wherein the test sample is a semen test sample.

3. The method of claim 1, wherein quantifying expression levels of HSFY comprises measuring HSFY by polymerase chain reaction (PCR), reverse transcription, quantitative reverse-transcriptase-polymerase-chain-reaction (RT-PCR), serial analysis of gene expression (SAGE), northern blot analysis, in situ hybridization, or combinations thereof.

4. The method of claim 1, wherein the housekeeping gene is ubiquitin C, beta-actin, GAPDH, 18S ribosomal RNA (18S rRNA), porphobilinogen-deaminase (PBGD) or a combination thereof.

5. The method of claim 1, wherein the HSFY quantified test result is a ratio of HSFY to PBGD expression levels.

6. The method of claim 1, wherein the baseline HFSY expression level is a quantified HSFY expression level, a ratio of HSFY to PBGD expression levels, a range of HSFY expression levels, or a range of ratios of HSFY to PBGD expression levels in a male, or in a collection of males, with nonobstructive azoospermia and/or AZFb microdeletions, where sperm retrieval was unsuccessful.

7. The method of claim 1, wherein the baseline HFSY expression level is a mean±95% confidence interval of a group of quantified HSFY expression values observed in males where sperm retrieval was not successful.

8. The method of claim 1, wherein the baseline HFSY expression level is a mean±95% confidence interval of a group of quantified HSFY expression values observed in males with nonobstructive azoospermia and with AZFb microdeletions.

9. The method of claim 1, wherein the HSFY quantified test result is compared with the baseline HFSY expression level using a computer, a processor, a data display and/or a data output.

* * * * *

UNITED STATES PATENT AND TRADEMARK OFFICE
CERTIFICATE OF CORRECTION

PATENT NO. : 10,822,657 B2
APPLICATION NO. : 14/005991
DATED : November 3, 2020
INVENTOR(S) : Stahl et al.

Page 1 of 1

It is certified that error appears in the above-identified patent and that said Letters Patent is hereby corrected as shown below:

On the Title Page

Item (54), in "Title", in Column 1, Line 2, after "SPERM", insert --¶(71) Applicant: Cornell University, Ithaca, NY (US)--

Item (56), in Column 2, under "Other Publications", Line 11, delete "Oct. 2412"," and insert --Oct. 24, 2012",-- therefor Item (56), in Column 2, under "Other Publications", Line 13, delete "Oct. 2412"," and insert --Oct. 24, 2012",-- therefor Signed and Sealed this
Second Day of February, 2021

Drew Hirshfeld
*Performing the Functions and Duties of the*
*Under Secretary of Commerce for Intellectual Property and*
*Director of the United States Patent and Trademark Office*